(12) United States Patent
Iimura et al.

(10) Patent No.: US 8,461,258 B2
(45) Date of Patent: Jun. 11, 2013

(54) METHOD OF PRODUCING AMINO ACID-MODIFIED ORGANOPOLYSILOXANE EMULSIONS

(75) Inventors: Tomohiro Iimura, Sodegaura (JP); Shinya Oguri, Ichihara (JP); Masaru Ozaki, Ichihara (JP); Tadashi Okawa, Ichihara (JP); Bethany Johnson, Midland, MI (US); Anne-Marie Vincent, Les Bons Villers (BE); Giada Tonet, Chapelle-les-Herlaimont (BE)

(73) Assignees: Dow Corning Toray Company, Ltd., Chiyoda-ku, Tokyo (JP); Dow Corning Corporation, Midland, MI (US); Dow Corning Europe SA, Seneffe (BE)

( * ) Notice: Subject to any disclaimer, the term of this patent is extended or adjusted under 35 U.S.C. 154(b) by 224 days.

(21) Appl. No.: 12/810,259

(22) PCT Filed: Dec. 25, 2008

(86) PCT No.: PCT/JP2008/073923
§ 371 (c)(1),
(2), (4) Date: Aug. 18, 2010

(87) PCT Pub. No.: WO2009/084711
PCT Pub. Date: Jul. 9, 2009

(65) Prior Publication Data
US 2010/0310496 A1 Dec. 9, 2010

(30) Foreign Application Priority Data
Dec. 27, 2007 (JP) .................. 2007-337998

(51) Int. Cl.
*C08G 77/26* (2006.01)
(52) U.S. Cl.
USPC .................. 524/838; 528/26; 528/28
(58) Field of Classification Search
USPC .................. 524/838; 528/26, 28
See application file for complete search history.

(56) References Cited

U.S. PATENT DOCUMENTS

| | | | |
|---|---|---|---|
| 4,980,167 A | 12/1990 | Harashima et al. | |
| 5,679,819 A * | 10/1997 | Jones et al. | 556/418 |
| 5,753,214 A * | 5/1998 | Yoshioka et al. | 424/70.2 |
| 6,358,501 B1 * | 3/2002 | Dietz et al. | 424/70.12 |
| 6,989,437 B2 * | 1/2006 | Van Dyke | 530/357 |

FOREIGN PATENT DOCUMENTS

| | | |
|---|---|---|
| DE | 10036532 A1 | 2/2002 |
| EP | 1149855 A1 | 10/2001 |
| JP | 50-158700 A | 12/1975 |
| JP | 52-003023 A | 1/1977 |
| JP | 52-114699 A | 9/1977 |
| JP | 02-243612 A | 9/1990 |
| JP | 08-012524 A | 1/1996 |
| JP | 08-012545 A | 1/1996 |
| JP | 08-012546 A | 1/1996 |
| JP | 09-241511 A | 9/1997 |
| JP | 10-036219 A | 2/1998 |
| JP | 11-193331 A | 7/1999 |
| JP | 2000-063225 A | 2/2000 |
| JP | 2000-281523 A | 10/2000 |
| JP | 2003-226611 A | 8/2003 |

OTHER PUBLICATIONS

English language abstract for DE 10036532, extracted from espacenet.com database, dated Jun. 28, 2010, 9 pages.
English language abstract for JP 50-158700, 8 pages.
English language abstract for JP 52-003023, extracted from PAJ database, dated Jun. 7, 2010, 7 pages.
English language abstract for JP 52-114699, extracted from PAJ database, dated Jun. 7, 2010, 5 pages.
English language abstract for JP 02-243612, extracted from espacenet.com database, dated Jun. 28, 2010, 9 pages.
English language translation and abstract for JP 08-012524, extracted from PAJ database, dated Jun. 28, 2010, 33 pages.
English language translation and abstract for JP 08-012545, extracted from PAJ database, dated Jun. 28, 2010, 30 pages.
English language translation and abstract for JP 08-012546, extracted from PAJ database, dated Jun. 28, 2010, 32 pages.
English language translation and abstract for JP 09-241511, extracted from PAJ database, dated Jun. 28, 2010, 35 pages.
English language translation and abstract for JP 10-036219, extracted from PAJ database, dated Jun. 29, 2010, 43 pages.
English language translation and abstract for JP 11-193331, extracted from PAJ database, dated Jun. 29, 2010, 59 pages.
English language translation and abstract for JP 2000-063225, extracted from PAJ database, dated Jun. 29, 2010, 75 pages.
English language translation and abstract for JP 2000-281523, extracted from PAJ database, dated Jun. 29, 2010, 109 pages.
English language translation and abstract for JP 2003-226611, extracted from PAJ database, dated Jun. 29, 2010, 81 pages.
PCT International Search Report for PCT/JP2008/073923, dated Apr. 9, 2009, 3 pages.

* cited by examiner

*Primary Examiner* — Margaret Moore
(74) *Attorney, Agent, or Firm* — Howard & Howard Attorneys PLLC

(57) ABSTRACT

The present invention relates to an amino acid-modified organopolysiloxane emulsion obtainable by reacting (a) a carboxy-unprotected amino acid, and (b) organopolysiloxane having an epoxy group in the molecule in an aqueous medium in the presence of a surfactant, is incorporated in a cosmetic product. The present invention also relates to the simple and highly efficient production of emulsions of amino acid-modified polysiloxane, as well as the use of the emulsions as beautifying components.

12 Claims, 2 Drawing Sheets

METHOD OF PRODUCING AMINO ACID-MODIFIED ORGANOPOLYSILOXANE EMULSIONS

RELATED APPLICATIONS

This application claims priority to and all the advantages of International Patent Application No. PCT/JP2008/073923, filed on Dec. 25, 2008, which claims priority to Japanese Patent Application No. JP 2007-337998, filed on Dec. 27, 2007.

TECHNICAL FIELD

The present invention relates to a basic amino acid-modified organopolysiloxane useful as a beautifying component for incorporation into cosmetic products. The present invention additionally relates to a method of producing this basic amino acid-modified organopolysiloxane and to the application of this basic amino acid-modified organopolysiloxane to cosmetic products.

Priority is claimed on Japanese Patent Application No. 2007-337998, filed on Dec. 27, 2007, the content of which is incorporated herein by reference.

BACKGROUND ART

Methods for producing amino acid-modified organopolysiloxanes can be exemplified by a method in which an N-acylamino acid is reacted in a polar aprotic solvent with an organopolysiloxane that contains a halogenated alkyl group in the molecule (refer to JP 50-158700 A); a method in which an amino acid is reacted in the presence of an acid catalyst with organopolysiloxane that has a carbon-bonded hydroxyl group in the molecule (refer to JP 52-003023 A); and a method in which a carboxy-protected amino acid is reacted with an organopolysiloxane that has an epoxy group in the molecule (refer to JP 52-114699 A).

However, a problem with the methods provided in JP 50-158700 A and JP 52-003023 A is that no carboxy group of amino acid origin remains in the obtained amino acid-modified organopolysiloxane due to the reaction of the carboxy group in the amino acid, resulting in an inability to impart the properties characteristic of amino acids to this organopolysiloxane. The method provided in JP 52-114699 A requires that the carboxy group of the amino acid be protected as an alkali metal salt or ester, and also requires removal of the alkali metal or alcohol from the reaction product.

Moreover, while the use of amino acid-modified organopolysiloxane as a surfactant is disclosed in JP 50-158700 A, JP 52-003023 A, and JP 52-114699 A, there is no recognition therein with regard to the function of the amino acid-modified organopolysiloxane itself as a beautifying agent.

DISCLOSURE OF INVENTION

The present invention was accomplished in view of the current circumstances as described above, and one objective is highly efficient provision of amino acid-modified organopolysiloxane by a simple method. An additional objective of the present invention is the utilization of this amino acid-modified organopolysiloxane as a beautifying agent.

The objectives of the present invention are achieved by producing an amino acid-modified organopolysiloxane by reacting, in an aqueous medium in the presence of a surfactant, (a) a carboxy-unprotected amino acid and (b) organopolysiloxane that has an epoxy group in the molecule, and by incorporating the resulting amino acid-modified organopolysiloxane emulsion in a cosmetic product.

The carboxy-unprotected amino acid (a) is preferably a basic amino acid selected from the group consisting of lysine, arginine, and histidine and particularly preferably is arginine as represented by the following formula:

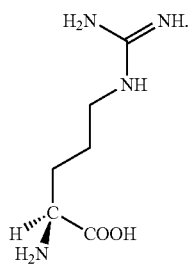

The organopolysiloxane that has an epoxy group in the molecule (b) is preferably organopolysiloxane represented by the following general formula (1):

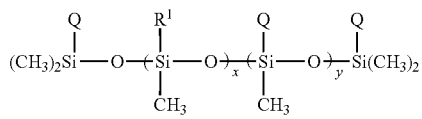

{wherein
each $R^1$ independently represents unsubstituted or substituted alkyl, unsubstituted or substituted aryl, unsubstituted or substituted aralkyl, unsubstituted or substituted alkoxy, an unsubstituted or substituted polyether group, hydroxyl, -A-NH—B—NH$_2$, -A-N(—B—NH$_2$)$_2$, or —CH$_2$CH$_2$Si(CH$_3$)$_2$—{OSi(CH$_3$)$_2$}$_t$—OSi(CH$_3$)$_3$ (in these formulas, A and B each independently represent unsubstituted or substituted alkylene or —C$_u$H$_{2u}$—O—C$_v$H$_{2v}$— (u and v each independently represent an integer in the range from 1 to 5) and t represents an integer in the range from 0 to 500);
Q is a group represented by the following formula

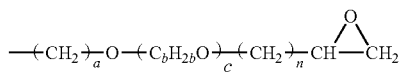

(wherein a represents an integer in the range from 1 to 20, b represents an integer in the range from 1 to 10, c represents an integer in the range from 0 to 50, and n represents an integer in the range from 1 to 20), or represents a group as defined for $R^1$ above, with the proviso that all of the Q groups are not $R^1$;
x represents an integer in the range from 1 to 10000; and
y represents an integer in the range from 0 to 1000},
or is represented by the following general formula (2):

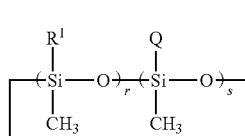

(wherein
R$^1$ and Q are defined as above;
r represents an integer in the range from 1 to 10;
s represents an integer in the range from 1 to 10; and
r+s represents an integer in the range from 3 to 20).

The organopolysiloxane that has an epoxy group in the molecule (b) is more preferably organopolysiloxane that has an epoxy group and an ether chain in the molecule and is represented by the following general formula (1'):

$$(CH_3)_3Si-O \overbrace{-Si-O-}^{Q'}_{x'} \overbrace{-Si-O-}^{Q'}_{y'} Si(CH_3)_3 \quad (1')$$
$$\qquad\qquad\qquad CH_3 \qquad\quad CH_3$$

with $R^{1'}$ on the middle Si and $Q'$ on the others (as shown).

{wherein
each R$^{1'}$ independently represents unsubstituted or substituted C$_{1-20}$ alkyl, unsubstituted or substituted C$_{6-20}$ aryl, unsubstituted or substituted C$_{7-20}$ aralkyl, or hydroxyl;
Q' is a group represented by $$-(CH_2)_a-O-\left(\begin{array}{c}CH_3\\|\\CH_2CHO\end{array}\right)_d-(CH_2CH_2O)_e-(CH_2)_n-HC\overset{O}{\underset{}{\diagdown}}CH_2$$

(wherein
n and a are defined as above,
d represents an integer in the range from 0 to 10, and
e represents an integer in the range from 0 to 10), or represents a group as defined for R$^{1'}$ above, with the proviso that all of the Q' groups are not R$^{1'}$;
x' represents an integer in the range from 5 to 1000; and
y' represents an integer in the range from 0 to 100}.

The surfactant is preferably selected from the group consisting of nonionic surfactants, anionic surfactants, and their mixtures or from the group consisting of nonionic surfactants, cationic surfactants, and their mixtures.

The amino acid-modified organopolysiloxane emulsion according to the present invention comprises:
(A) amino acid-modified organopolysiloxane that has in the molecule at least one moiety represented by the following formula (3), (4), or (5);

$$-(CH_2)_n-\overset{OH}{\underset{|}{CH}}-CH_2-\overset{H}{\underset{|}{N}}- \quad (3)$$

$$-(CH_2)_n-\overset{OH}{\underset{|}{CH}}-CH_2-N\diagup\diagdown \quad (4)$$

$$-(CH_2)_n-\overset{OH}{\underset{|}{CH}}-CH_2-N\overset{\diagup}{\underset{\diagdown}{\cdot\cdot}} \quad (5)$$

(wherein in these formulas,
n is defined as above, and
N represents a nitrogen atom originating from the carboxy-unprotected amino acid (a) and the $$-N\overset{\diagup}{\underset{\diagdown}{\cdot\cdot}}$$

in formula (5) indicates that the N participates in an aromatic heterocyclic ring);
(B) surfactant; and
(C) water.

The carboxy-unprotected amino acid (a) is preferably a basic amino acid selected from the group consisting of lysine, arginine, and histidine.

The amino acid-modified organopolysiloxane (A) is preferably represented by the following general formula (3'):

$$Z-(CH_2)_n-\overset{OH}{\underset{|}{CH}}-CH_2-\overset{H}{\underset{|}{N}}-R^2 \quad (3')$$

{wherein
Z represents an organopolysiloxane residue;
R$^2$ represents
—CH(COOH)—(CH$_2$)$_3$—NH—C(=NH)—NH$_2$,
—C(=NH)—NH—(CH$_2$)$_3$—CH(COOH)—NH$_2$,
—CH(COOH)—(CH$_2$)$_3$—N(—CH$_2$—CH(OH)—(CH$_2$)—C(=NH)—NH$_2$,
—C(=NH)—N(—CH$_2$—CH(OH)—(CH$_2$)$_{n'}$—Z')—(CH$_2$)$_3$—CH(COOH)—NH$_2$,
—C(=NH)—NH—(CH$_2$)$_3$—CH(COOH)—NH—CH$_2$—CH(OH)—(CH$_2$)$_{n'}$—Z',
—CH(COOH)—(CH$_2$)$_3$—N(—CH$_2$—CH(OH)—(CH$_2$)$_{n'}$—Z')—C(=NH)—NH—CH(OH)—CH$_2$)$_{n''}$—Z'',
—C(=NH)—NH—(CH$_2$)$_3$—CH(COOH)—N(—CH$_2$—CH(OH)—(CH$_2$)$_{n'}$—Z')—CH$_2$—CH(OH)—(CH$_2$)$_{n''}$—Z'',
—CH(COOH)—(CH$_2$)$_3$—NH—C(=NH)—N(—CH$_2$—CH(OH)—(CH$_2$)$_{n'}$—Z')—CH(OH)—(CH$_2$)$_{n''}$—Z'',
—C(=NH)—N(—CH$_2$—CH(OH)—(CH$_2$)$_{n'''}$—Z''')—(CH$_2$)$_3$—CH(COOH)—N(—CH$_2$—CH(OH)—(CH$_2$)$_{n'}$—Z')—CH$_2$—CH(OH)—(CH$_2$)$_{n''}$—Z'',
—CH(COOH)—(CH$_2$)$_3$—N(—CH$_2$—CH(OH)—(CH$_2$)$_{n'''}$—Z''')—C(=NH)—N(—CH$_2$—CH(OH)—(CH$_2$)$_{n'}$—Z')—CH(OH)—(CH$_2$)$_{n''}$—Z'',
—(CH$_2$)$_4$—CH(NH$_2$)COOH,
—CH(COOH)—(CH$_2$)$_4$—NH$_2$,
—(CH$_2$)$_4$—CH(NH—CH$_2$—CH(OH)—(CH$_2$)$_{n'}$—Z')COOH,
—(CH$_2$)$_4$—CH(N(—CH$_2$—CH(OH)—(CH$_2$)$_{n'}$—Z')—CH$_2$—CH(OH)—(CH$_2$)$_{n''}$—Z''),
—CH(COOH)—(CH$_2$)$_4$—N(—CH$_2$—CH(OH)—(CH$_2$)$_{n'}$—Z')—CH$_2$—CH(OH)—(CH$_2$)$_{n''}$—Z'', or
—CH(COOH)—CH$_2$-imidazolyl
(wherein in the preceding formulas
Z', Z'', and Z''' each independently represent an organopolysiloxane residue, and n', n'', and n''' each independently represent an integer in the range from 1 to 20); and
n is defined as above},
or the following general formula (4'):

$$Z\!-\!(CH_2)_{\overline{n}}\!-\!\underset{\underset{\displaystyle OH}{|}}{CH}\!-\!CH_2\!-\!N\!\!\begin{array}{c}R^3\\ \\R^4\end{array} \quad (4')$$

{wherein
Z is defined as above;
$R^3$ represents
—CH(COOH)—(CH$_2$)$_3$—NH—C(=NH)—NH$_2$,
—C(=NH)—NH—(CH$_2$)$_3$—CH(COOH)—NH$_2$,
—(CH$_2$)$_3$—CH(COOH)—NH$_2$,
—CH(COOH)—(CH$_2$)$_3$—N(—CH$_2$—CH(OH)—(CH$_2$)$_{n'}$—Z')—C(=NH)—NH$_2$,
—C(=NH)—N(—CH$_2$—CH(OH)—(CH$_2$)$_{n'}$—Z')—(CH$_2$)$_3$—CH(COOH)—NH$_2$,
—CH(COOH)—(CH$_2$)$_3$—NH—C(=NH)—N(—CH$_2$—CH(OH)—(CH$_2$)$_{n'}$—Z')—CH$_2$—CH(OH)—(CH$_2$)$_{n''}$—Z'',
—C(=NH)—N(—CH$_2$—CH(OH)—(CH$_2$)$_{n'}$—Z')—(CH$_2$)$_3$—CH(COOH)—N(—CH$_2$—CH(OH)—(CH$_2$)$_{n''}$—Z'')—CH$_2$—CH(OH)—(CH$_2$)$_{n'''}$—Z''',
—(CH$_2$)$_4$—CH(NH$_2$)COOH,
—CH(COOH)—(CH$_2$)$_4$—NH$_2$,
—CH(COOH)—(CH$_2$)$_4$—N(—CH$_2$—CH(OH)—(CH$_2$)$_{n'}$—Z')—CH$_2$—CH(OH)—(CH$_2$)$_{n''}$—Z'', or
—CH(COOH)—CH$_2$-imidazolyl
(wherein in the preceding formulas Z', Z'', and Z''' and n', n'', and n''' are defined as above);
$R^4$ represents
—C(=NH)—NH$_2$ or
—CH$_2$—CH(OH)—(CH$_2$)$_{n''''}$—Z''''
(wherein in the preceding formulas
Z'''' represents a polysiloxane residue, and
n'''' represents an integer in the range from 1 to 20); and
n is defined as above},
or the following general formula (5'):

$$Z\!-\!(CH_2)_{\overline{n}}\!-\!\underset{\underset{\displaystyle OH}{|}}{CH}\!-\!CH_2\!-\!N\!\!\underset{R^5}{\overset{}{\diagup\!\!\diagdown\!\!N}} \quad (5')$$

{wherein
Z is defined as above;
$R^5$ represents
—CH$_2$—CH(NH$_2$)COOH,
—CH$_2$—CH(NH(—CH$_2$—CH(OH)—(CH$_2$)$_{n'}$—Z'))COOH, or
—CH$_2$—CH(N(—CH$_2$—CH(OH)—(CH$_2$)$_{n'}$—Z')—CH$_2$—CH(OH)—(CH$_2$)$_{n''}$—Z'')COOH
(wherein in the preceding formulas
Z' and Z'' and n' and n'' are defined as above); and
n is defined as above}.

The above-cited organopolysiloxane residue can be represented by the following general formula (6):

$$(CH_3)_2Si\!-\!O\!-\!\!\left(\!\underset{\underset{\displaystyle CH_3}{|}}{\overset{\overset{\displaystyle R^1}{|}}{Si}}\!-\!O\!\right)_{\!x}\!\!\left(\!\underset{\underset{\displaystyle CH_3}{|}}{\overset{\overset{\displaystyle D}{|}}{Si}}\!-\!O\!\right)_{\!y}\!\!\underset{}{\overset{\overset{\displaystyle D}{|}}{Si}}(CH_3)_2 \quad (6)$$

{wherein
$R^1$ is defined as above;
D represents —(CH$_2$)$_a$—O—(C$_b$H$_{2b}$O)$_c$— (wherein a, b, and c are defined as above), or a group as defined for $R^1$ above, with the proviso that all of the D groups are not $R^1$; and
x and y are defined as above), or
by the following general formula (7):

$$\left[\!\!\underset{\underset{\displaystyle CH_3}{|}}{\overset{\overset{\displaystyle R^1}{|}}{Si}}\!-\!O\!\right]_{\!r}\!\!\left[\!\underset{\underset{\displaystyle CH_3}{|}}{\overset{\overset{\displaystyle D}{|}}{Si}}\!-\!O\!\right]_{\!s} \quad (7)$$

(wherein $R^1$, D, r, and s are defined as above and r+s represents an integer in the range from 3 to 20).

More preferably, the amino acid-modified organopolysiloxane (A) has, in its molecule, at least one moiety represented by the following formula (3''), (4''), or (5''):

$$-\!(CH_2)_{\overline{a}}\!-\!O\!-\!\!\left(\!CH_2\!-\!\underset{\underset{\displaystyle CH_3}{|}}{CH}\!O\!\right)_{\!d}\!\!(CH_2CH_2O)_{\overline{e}}\!(CH_2)_{\overline{n}}\!-\!\underset{\underset{\displaystyle OH}{|}}{CH}\!-\!CH_2\!-\!\underset{\underset{\displaystyle H}{|}}{N}\!-\! \quad (3'')$$

$$-\!(CH_2)_{\overline{a}}\!-\!O\!-\!\!\left(\!CH_2\!-\!\underset{\underset{\displaystyle CH_3}{|}}{CH}\!O\!\right)_{\!d}\!\!(CH_2CH_2O)_{\overline{e}}\!(CH_2)_{\overline{n}}\!-\!\underset{\underset{\displaystyle OH}{|}}{CH}\!-\!CH_2\!-\!\underset{\underset{\displaystyle H}{|}}{N}\!-\!N\!\!\begin{array}{c}\diagup\\\diagdown\end{array} \quad (4'')$$

$$-\!(CH_2)_{\overline{a}}\!-\!O\!-\!\!\left(\!CH_2\!-\!\underset{\underset{\displaystyle CH_3}{|}}{CH}\!O\!\right)_{\!d}\!\!(CH_2CH_2O)_{\overline{e}}\!(CH_2)_{\overline{n}}\!-\!\underset{\underset{\displaystyle OH}{|}}{CH}\!-\!CH_2\!-\!\underset{\underset{\displaystyle H}{|}}{N}\!-\!N\!\!\begin{array}{c}\diagup\\\!\!\!\!\diagdown\end{array} \quad (5'')$$

(n, a, d, and e in these formulas are defined as above).

An arginine-modified organopolysiloxane represented by the following general formula (8):

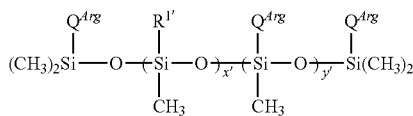

{wherein
R$^{1'}$ is defined as above;
Q$^{Arg}$ is a group represented by the following formula:

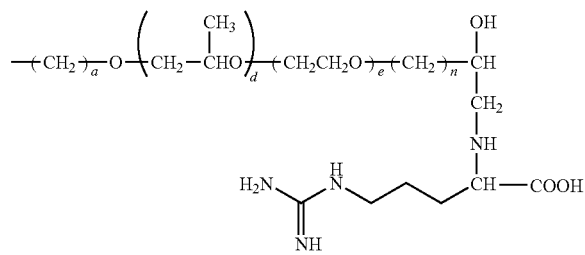

(wherein n, a, d, and e are defined as above), or represents a group as defined for R$^{1'}$ above, with the proviso that all of the Q$^{Arg}$ groups are not R$^{1'}$; and
x' and y' are defined as above}
is particularly preferred for the amino acid-modified organopolysiloxane (A).

The amino acid-modified organopolysiloxane emulsion preferably comprises 1 to 100 parts by weight of the surfactant (B) and 10 to 10,000 parts by weight of water (C), in each case with reference to 100 parts by weight of the amino acid-modified organopolysiloxane (A).

The amino acid-modified organopolysiloxane emulsion as described hereinabove is useful as a raw material for cosmetic products, and therefore it can be used by being incorporated into cosmetic products.

The production method of the present invention, because it does not require that the carboxy group of the amino acid be protected in the form of an alkali metal salt or an ester, is able to very efficiently produce an emulsion that contains amino acid-modified organopolysiloxane, and is able to do so by a simple procedure. In addition, the emulsion under consideration is immediately usable because there is no necessity to remove an alkali metal or an alcohol from the amino acid-modified organopolysiloxane after production.

The amino acid-modified organopolysiloxane according to the present invention is useful as an ingredient for cosmetic products; for example, it can be incorporated into a cosmetic product as a beautifying agent such as a conditioning agent.

BEST MODE FOR CARRYING OUT THE INVENTION

Figure 1:
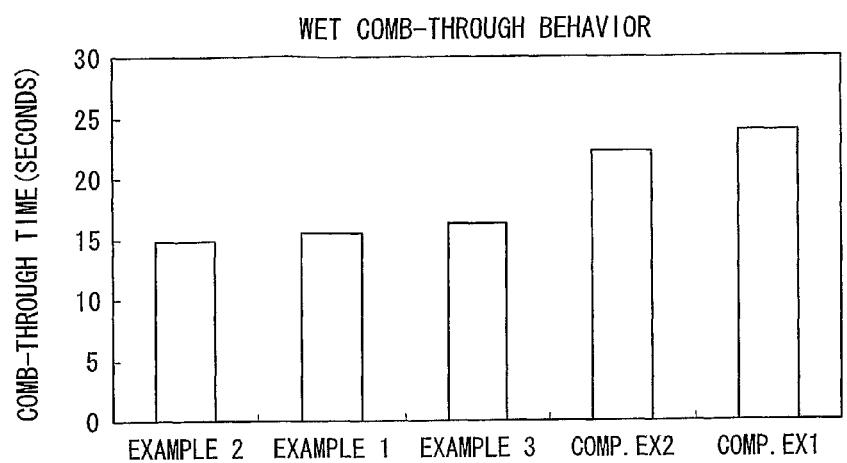
FIG. 1 is a graph showing the results of the evaluation of wet combability of Examples 1 to 3 and Comparative Examples 1 and 2.

The method of the present invention for producing amino acid-modified organopolysiloxane emulsions is characterized by reacting
(a) a carboxy-unprotected amino acid, and
(b) organopolysiloxane that has an epoxy group in the molecule in an aqueous medium in the presence of a surfactant.

In the present invention, "carboxy-unprotected amino acid" means that a carboxy group that is necessarily present in an amino acid is not protected in the form of an ester or a salt, but rather is in the —COOH form. Although there is a hydrogen atom present on both the carboxy group (—COOH) and the primary amino group (—NH$_2$) or secondary amino group (—NH—) in the carboxy-unprotected amino acid (a) used in the production method of the present invention, only the primary amino group or secondary amino group selectively reacts with the epoxy group in the epoxy-functional organopolysiloxane (b). The production method of the present invention therefore does not require that the carboxy group of an amino acid used as a raw material be protected, for example, by esterification.

Thus, the production method of the present invention can directly use an amino acid as the "(a) carboxy-unprotected amino acid", as a raw material, and does not require a protection step (for example, esterification) for the carboxy group of the amino acid, and as a result is able to very efficiently produce an emulsion that contains amino acid-modified organopolysiloxane, and is able to do so by a simple procedure. Moreover, unlike when a carboxy-protected amino acid is used as a raw material, deprotection need not be carried out after synthesis of the amino acid-modified organopolysiloxane, which enables a major simplification of the process of producing amino acid-modified organopolysiloxane, and also enables the direct and immediate use of the resulting amino acid-modified organopolysiloxane emulsion.

The reaction between the carboxy-unprotected amino acid (a) and the epoxy-functional organopolysiloxane (b) can be readily carried out by mixing desired quantities of these reactants in an aqueous medium together with a surfactant. The mixing means is not particularly limited and simple, well-known stirring devices or mixers can be used, for example, a paddle-equipped stirrer, propeller stirrer, Henschel mixer, TK Homo Mixer (Tokushu Kika Kogyo Kabushiki Kaisha), TK Homo Disper (Tokushu Kika Kogyo Kabushiki Kaisha), and so forth.

However, in order to accelerate the emulsification function exhibited by the surfactant, a high shear force emulsifying device, such as a colloid mill or colloid mixer, or a high-pressure emulsifying device is preferably used. A high-pressure emulsifying device is a device whose purpose is to bring about the formation of a homogeneous emulsion by microfine-sizing the organopolysiloxane present in a primary emulsion by means of ultrasound, turbulent flow, cavitation, shear force, or an impact force generated by pressurizing the primary emulsion within the device to create a high velocity flow and either splitting this flow and then causing the split flows to impact with one another or passing it across an adjusted microfine gap and impacting it on an impact ring or rotor. Specific examples are an ultrahigh-pressure Gaulin model homogenizer (Gaulin Co.), high-pressure homogenizers from Izumi Food Machinery Co., Ltd., high-pressure homogenizers from Rannie, Microfluidizers (Microfluidics), the Nanomizer (Nanomizer Co., Ltd.), and so forth.

There are no particular limitations on the carboxy-unprotected amino acid (a) used by the present invention as long as it has both an amino group and a carboxy group. However, basic amino acids selected from the group consisting of lysine, arginine, and histidine are preferred. Arginine is particularly preferred as the basic amino acid.

There are no particular limitations on the above-cited epoxy-functional organopolysiloxane (b) as long as it is organopolysiloxane containing at least one epoxy group. However, a preferred organopolysiloxane is represented by the following general formula (1):

$$(CH_3)_2\overset{Q}{\underset{|}{Si}}-O-\left(\overset{R^1}{\underset{\underset{CH_3}{|}}{Si}}-O\right)_x\left(\overset{Q}{\underset{\underset{CH_3}{|}}{Si}}-O\right)_y\overset{Q}{\underset{|}{Si}}(CH_3)_2 \tag{1}$$

{wherein
each $R^1$ independently represents unsubstituted or substituted alkyl, unsubstituted or substituted aryl, unsubstituted or substituted aralkyl, unsubstituted or substituted alkoxy, an unsubstituted or substituted polyether group, hydroxyl, -A-NH—B—$NH_2$, -A-N(—B—$NH_2$)$_2$, or —$CH_2CH_2Si$($CH_3$)$_2$—{$OSi(CH_3)_2$}$_t$—$OSi(CH_3)_3$ (in these formulas, A and B each independently represent unsubstituted or substituted alkylene or —$C_uH_{2u}$—O—$C_vH_{2v}$— (u and v each independently represent an integer in the range from 1 to 5) and t represents an integer in the range from 0 to 500);
Q is a group represented by the following formula $$-(CH_2)_a-O-(C_bH_{2b}O)_c-(CH_2)_n-CH\overset{O}{\underset{\diagdown}{\diagup}}CH_2$$

(wherein a represents an integer in the range from 1 to 20, b represents an integer in the range from 1 to 10, c represents an integer in the range from 0 to 50, and n represents an integer in the range from 1 to 20); or represents a group as defined for $R^1$ above, with the proviso that all of the Q groups are not $R^1$;
x represents an integer in the range from 1 to 10000; and
y represents an integer in the range from 0 to 10001, or is represented by the following general formula (2):

$$\boxed{\left(\overset{R^1}{\underset{\underset{CH_3}{|}}{Si}}-O\right)_r\left(\overset{Q}{\underset{\underset{CH_3}{|}}{Si}}-O\right)_s} \tag{2}$$

(wherein
$R^1$ and Q are defined as above;
r represents an integer in the range from 1 to 10;
s represents an integer in the range from 1 to 10; and
r+s represents an integer in the range from 3 to 20).

The alkyl is preferably $C_{1-20}$ alkyl, as exemplified by straight-chain alkyl groups and branched alkyl groups such as methyl, ethyl, n-propyl, isopropyl, n-butyl, isobutyl, sec-butyl, tert-butyl, pentyl, hexyl, heptyl, octyl, nonyl, decyl, and so forth. Methyl is particularly preferred as the alkyl group.

The alkyl may have a cyclic structure. $C_{3-6}$ cycloalkyl is very suitable as the alkyl having a cyclic structure, as exemplified by cyclopropyl, cyclopentyl, cyclohexyl, and so forth.

The cycloalkyl group may occur in a form combined with a straight-chain or branched alkyl group as described above, for example, cyclopropylmethyl, cyclobutylmethyl, cyclopentylmethyl, cyclohexylmethyl, and so forth.

The aryl is preferably $C_{6-20}$ aryl, for example, phenyl, tolyl, xylyl, and so forth. Phenyl is particularly preferred.

The aralkyl is preferably $C_{7-20}$ aralkyl, and has a structure in which the alkyl is combined with the aryl. The aralkyl is exemplified by benzyl, phenethyl, diphenylmethyl, and so forth. Benzyl is particularly preferred.

The alkoxy is preferably $C_{1-20}$ alkoxy, and has a structure in which the alkyl is combined with an oxy group (—O—). The alkoxy is exemplified by methoxy, ethoxy, n-propoxy, isopropoxy, n-butoxy, isobutoxy, sec-butoxy, tert-butoxy, pentoxy, and so forth. Methoxy is particularly preferred.

The polyether group is a group represented by —O($C_{v'}H_{2v'}$O)$_{u'}R^6$ (wherein v' is an integer from 2 to 4, u' is an integer with a value of at least 4, and $R^6$ represents a hydrogen atom or an alkyl group as described above). A polyoxyethylene group, a polyoxypropylene group, and a polyoxyethylenepolyoxyproplylene group are preferred.

The alkylene is preferably $C_{1-10}$ alkylene, and can be exemplified by methylene, ethylene, propylene, butylene, and so forth.

The hydrogen on the carbon in the alkyl, aryl, aralkyl, alkoxy, polyether group, and alkylene may be substituted by one or more substituents. These substituents are selected from halogen (fluorine, chlorine, bromine, and iodine) and a hydroxyl group.

The above-described epoxy-functional organopolysiloxane (b) preferably has an ether chain, and more preferably is organopolysiloxane that has an epoxy group and an ether chain in the molecule, and that is represented by the following general formula (1'):

$$(CH_3)_2\overset{Q'}{\underset{|}{Si}}-O-\left(\overset{R^{1'}}{\underset{\underset{CH_3}{|}}{Si}}-O\right)_{x'}\left(\overset{Q'}{\underset{\underset{CH_3}{|}}{Si}}-O\right)_{y'}\overset{Q'}{\underset{|}{Si}}(CH_3)_2 \tag{1'}$$

{wherein
each $R^{1'}$ independently represents unsubstituted or substituted $C_{1-20}$ alkyl, unsubstituted or substituted $C_{6-20}$ aryl, unsubstituted or substituted $C_{7-20}$ aralkyl, or hydroxyl;
Q' is a group represented by $$-(CH_2)_a-O-\left(\overset{CH_3}{\underset{|}{CH_2CHO}}\right)_d-(CH_2CH_2O)_e-(CH_2)_n-HC\overset{O}{\underset{\diagdown}{\diagup}}CH_2$$

(wherein
n and a are defined as above,
d represents an integer in the range from 0 to 10,
e represents an integer in the range from 0 to 10, and
d+e≧1), or represents a group as defined for $R^{1'}$ above, with the proviso that all of the Q' groups are not $R^{1'}$;
x' represents an integer in the range from 5 to 1000; and
y' represents an integer in the range from 0 to 100}.
This ether chain is preferably a polyether chain. d+e≧1 is therefore preferred in the formula given above.

The surfactant used in the present invention is not particularly limited, and any surfactant, i.e., anionic, cationic, amphoteric, or nonionic, can be used. A single surfactant can be used, or two or more may be used in combination.

Examples of the anionic surfactant include saturated and unsaturated higher fatty acid salts (e.g., sodium laurate, sodium stearate, sodium oleate, sodium linolenate, and so forth), long-chain alkyl sulfuric acid salts, alkylbenzenesulfonic acids (e.g., hexylbenzenesulfonic acid, octylbenzenesulfonic acid, dodecylbenzenesulfonic acid, and so forth) and their salts, polyoxyalkylene alkyl ether sulfates, polyoxyalkylene alkenyl ether sulfates, polyoxyethylene alkyl sulfate ester salts, the salts of alkyl sulfosuccinate esters, polyoxyalkylene sulfosuccinate salts, polyoxyalkylene sulfosuccinate alkyl ester salts, the alkali metal salts of the sulfosuccinic acid esters of polyoxyalkylene-modified dimethylpolysiloxane, polyoxyalkylene alkylphenyl ether sulfates, long-chain alkanesulfonic acid salts, long-chain alkylsulfonates, polyoxyethylene alkylphenyl ether sulfates, polyoxyalkylene alkyl ether acetates, long-chain alkyl phosphate salts, polyoxyalkylene alkyl ether phosphate salts, acylglutamic acid salts, α-acylsulfonic acid salts, long-chain alkylsulfonic acid salts, alkylallylsulfonic acid salts, long-chain α-olefinsulfonates, alkylnaphthalenesulfonic acid salts, long-chain alkanesulfonic acid salts, long-chain alkyl or alkenyl sulfate salts, long-chain alkylamide sulfate salts, long-chain alkyl or alkenyl phosphate salts, alkylamide phosphates, alkyloylalkyltaurine salts, N-acylamino acid salts, sulfosuccinic acid salts, alkyl alkylether carboxylic acid salts, amide ether carboxylates, α-sulfofatty acid ester salts, alanine derivatives, glycine derivatives, arginine derivatives, and so forth. The aforementioned salts can be exemplified by the alkali metal salts, e.g., sodium, potassium, and so forth; alkanolamine salts such as triethanolamine salt and so forth; and ammonium salts; wherein the sodium salts are preferred.

Examples of the cationic surfactants include alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, octyltrimethylammonium hydroxide, dodecyltrimethylammonium hydroxide, stearyltrimethylammonium bromide, behenyltrimethylammonium bromide, distearyldimethylammonium chloride, dicocoyldimethylammonium chloride, dioctyldimethylammonium chloride, di(POE)oleylmethylammonium chloride (2EO), benzalkonium chloride, alkylbenzalkonium chloride, alkyldimethylbenzalkonium chloride, benzethonium chloride, stearyldimethylbenzylammonium chloride, lanolin-derived quaternary ammonium salts, stearic acid diethylaminoethylamide, stearic acid dimethylaminopropylamide, behenamidepropyldimethylhydroxypropylammonium chloride, stearoylcolaminoformylmethylpyridinium chloride, cetylpyridinium chloride, tall oil alkylbenzylhydroxyethylimidazolinium chloride, and benzyl ammonium salts.

The amphoteric surfactant is preferably a phospholipid. The phospholipids can be exemplified by lecithin, phosphatidylethanolamine, phosphatidic acid, phosphatidylinositol, phosphatidylserine, phosphatidylcholine, phosphatidylglycerol, sphingomyelin, cardiolipin, and hydrogenates of the preceding. Particularly preferred is the hydrogenated natural lecithin yielded by the hydrogenation of soy lecithin, egg yoke lecithin, corn lecithin, cotton seed oil lecithin, rapeseed lecithin, and so forth.

The nonionic surfactant can be exemplified by polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hydrogenated) castor oils, polyoxyalkylene alkylphenols, polyoxyalkylene alkylphenyl ethers, polyoxyalkylene phenylphenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycols, polyether-modified silicones (i.e., polyoxyalkylene-modified diorganopolysiloxanes), polyglyceryl-modified silicones, glyceryl-modified silicones, saccharide-modified silicones, perfluoropolyether-type surfactants, polyoxyethylene-polyoxypropylene block copolymers, and alkyl polyoxyethylene-polyoxypropylene block copolymer ethers.

The surfactant under consideration is preferably selected from the group consisting of nonionic surfactants, anionic surfactants, and their mixtures or from the group consisting of nonionic surfactants, cationic surfactants, and their mixtures.

The amino acid-modified organopolysiloxane emulsion of the present invention can be very suitably incorporated into skin cosmetic products when a nonionic surfactant, an anionic surfactant, or a mixture thereof is used as the surfactant.

The amino acid-modified organopolysiloxane emulsion of the present invention can be very suitably incorporated in hair cosmetic products when nonionic surfactant, cationic surfactant, or a mixture thereof is used as the surfactant.

The aqueous medium cited above is water or a mixture of water and a hydrophilic medium. The water should not contain a component injurious to the human body, should be pure, and can be exemplified by tap water, purified water, and mineral water. The hydrophilic medium can be exemplified by monohydric lower alcohols such as ethanol, n-propanol, isopropanol, n-butanol, and so forth; dihydric alcohols such as 1,3-butylene glycol, ethylene glycol, propylene. glycol, and so forth; polyalkylene glycols such as polyethylene glycol, dipropylene glycol, polypropylene glycol, and so forth; and polyhydric alcohols such as glycerol, diglycerol, trimethylolpropane, pentaerythritol, sorbitol, and so forth. A single hydrophilic medium may be used, or two or more hydrophilic media may be used in combination.

The amino acid-modified organopolysiloxane emulsion that can be obtained by the production method described above comprises (A) amino acid-modified organopolysiloxane that has in the molecule at least one moiety represented by the following formula (3), (4), or (5):

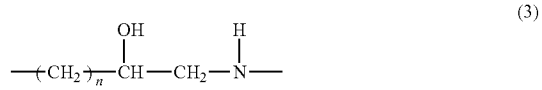

(3)

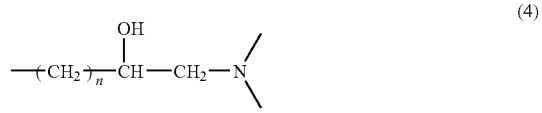

(4)

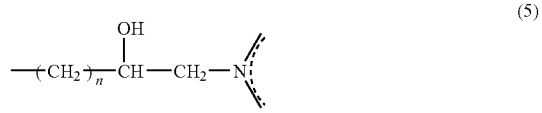

(5)

(wherein in these formulas,
n is defined as above, and
N represents a nitrogen atom originating from the carboxy-unprotected amino acid (a) and the

in formula (5) indicates that the N participates in an aromatic heterocyclic ring);
(B) surfactant; and
(C) water.

The amino acid-modified organopolysiloxane emulsion of the present invention very suitably contains 1 to 100 parts by weight, preferably 1 to 50 parts by weight, and more preferably 1 to 10 parts by weight of surfactant (B), in each case with reference to 100 parts by weight of the amino acid-modified organopolysiloxane (A), and 10 to 10000 parts by weight, preferably 100 to 10000 parts by weight, and more preferably 1000 to 10000 parts by weight of water (C), in each case with reference to 100 parts by weight of the amino acid-modified organopolysiloxane (A).

The amino acid-modified organopolysiloxane emulsion of the present invention is an oil-in-water type emulsion in which a discontinuous phase, comprising the amino acid-modified organopolysiloxane, is dispersed in a continuous phase comprising the aqueous medium. The discontinuous phase takes the form of particles, and the size of these particles is not particularly limited. However, the average particle size measured by laser diffraction/scattering is preferably no more than 100 μm, more preferably no more than 20 μm, more preferably no more than 10 μm, more preferably no more than 5 μm, more preferably no more than 1 μm, more preferably no more than 0.5 μm, and most preferably no more than 0.2 μm.

The carboxy-unprotected amino acid (a) described above is very suitably a basic amino acid selected from the group consisting of lysine, arginine, and histidine. In this case, the aromatic heterocycle in the aforementioned formula (5) is an imidazole ring originating with histidine. The carboxy group present in the lysine, arginine, and histidine is in the free form (—COOH), and is not in the salt form, nor is it esterified.

The amino acid-modified organopolysiloxane (A) is preferably represented by the following general formula (3'):

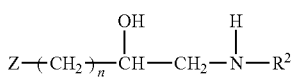

(3')

{wherein
Z represents an organopolysiloxane residue;
$R^2$ represents
—CH(COOH)—(CH$_2$)$_3$—NH—C(=NH)—NH$_2$,
—C(=NH)—NH—(CH$_2$)$_3$—CH(COOH)—NH$_2$,
—CH(COOH)—(CH$_2$)$_3$—N(—CH$_2$—CH(OH)—(CH$_2$)$_{n'}$—Z')—C(=NH)—NH$_2$,
—C(=NH)—N(—CH$_2$—CH(OH)—(CH$_2$)$_{n'}$—Z')—(CH$_2$)$_3$—CH(COOH)—NH$_2$,
—C(=NH)—NH—(CH$_2$)$_3$—CH(COOH)—NH—CH$_2$—CH(OH)—(CH$_2$)$_{n'}$—Z',
—CH(COOH)—(CH$_2$)$_3$—N(—CH$_2$—CH(OH)—(CH$_2$)$_{n'}$—Z')—C(=NH)—NH—CH(OH)—(CH$_2$)$_{n''}$—Z'',
—C(=NH)—NH—(CH$_2$)$_3$—CH(COOH)—N (—CH$_2$—CH(OH)—(CH$_2$)$_{n'}$—Z')—CH$_2$—CH(OH)—(CH$_2$)$_{n''}$—Z'',
—CH(COOH)—(CH$_2$)$_3$—NH—C(=NH)—N(—CH$_2$—CH(OH)—(CH$_2$)$_{n'}$—Z')—CH(OH)—(CH$_2$)$_{n''}$—Z'',
—C(=NH)—N(—CH$_2$—CH(OH)—(CH$_2$)$_{n'''}$—Z''')—(CH$_2$)$_3$—CH(COOH)—N(—CH$_2$—CH(OH)—(CH$_2$)$_{n'}$—Z')—CH$_2$—CH(OH)—(CH$_2$)$_{n''}$—Z'',
—CH(COOH)—(CH$_2$)$_3$—N(—CH$_2$—CH(OH)—(CH$_2$)$_{n'''}$—Z''')—C(=NH)—N(—CH$_2$—CH(OH)—(CH$_2$)$_{n'}$—Z')—CH(OH)—(CH$_2$)$_{n''}$—Z'',
—(CH$_2$)$_4$—CH(NH$_2$)COOH,
—CH(COOH)—(CH$_2$)$_4$—NH$_2$,
—(CH$_2$)$_4$—CH(NH—CH$_2$—CH(OH)—CH$_2$)$_{n'}$—Z')COOH,
—(CH$_2$)$_4$—CH(N(—CH$_2$—CH(OH)—(CH$_2$)$_{n'}$—Z')—CH$_2$—CH(OH)—(CH$_2$)$_{n''}$—Z''),
—CH(COOH)—(CH$_2$)$_4$—N(—CH$_2$—CH(OH)—(CH$_2$)$_{n'}$—Z')—CH$_2$—CH(OH)—(CH$_2$)$_{n''}$—Z'', or
—CH(COOH)—CH$_2$-imidazolyl
(wherein in the preceding formulas
Z', Z'', and Z''' each independently represent an organopolysiloxane residue, and
n', n'', and n''' each independently represent an integer in the range from 1 to 20); and
n is defined as above},
the following general formula (4'):

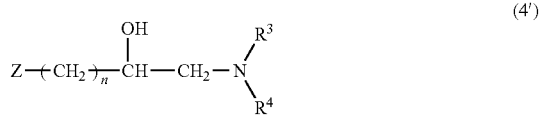

(4')

{wherein
Z is defined as above;
$R^3$ represents
—CH(COOH)—(CH$_2$)$_3$—NH—C(=NH)—NH$_2$,
—C(=NH)—NH—(CH$_2$)$_3$—CH(COOH)—NH$_2$,
—(CH$_2$)$_3$—OH(COOH)—NH$_2$,
—CH(COOH)—(CH$_2$)$_3$—N(—CH$_2$—CH(OH)—(CH$_2$)$_{n'}$—Z')—C(=NH)—NH$_2$,
—C(=NH)—N(—CH$_2$—CH(OH)—(CH$_2$)$_{n'}$—Z')—(CH$_2$)$_3$—CH(COOH)—NH$_2$,
—CH(COOH)—(CH$_2$)$_3$—NH—C(=NH)—N(—CH$_2$—CH(OH)—(CH$_2$)$_{n'}$—Z')—CH$_2$—CH(OH)—(CH$_2$)$_{n''}$—Z'',
—C(=NH)—N(—CH$_2$—CH(OH)—(CH$_2$)$_{n'}$—Z')—(CH$_2$)$_3$—CH(COOH)—N(—CH$_2$—CH(OH)—(CH$_2$)$_{n''}$—Z'')—CH$_2$—CH(OH)—(CH$_2$)$_{n'''}$—Z''',
—(CH$_2$)$_4$—CH(NH$_2$)COOH,
—CH(COOH)—(CH$_2$)$_4$—NH$_2$,
—CH(COOH)—(CH$_2$)$_4$—N(—CH$_2$—CH(OH)—(CH$_2$)$_{n'}$—Z')—CH$_2$—CH(OH)—(CH$_2$)$_{n''}$—Z'', or
—CH(COOH)—CH$_2$-imidazolyl
(wherein in the preceding formulas Z', Z'', and Z''' and n', n'', and n''' are defined as above);
$R^4$ represents
—C(=NH)—NH$_2$ or
—CH$_2$—CH(OH)—(CH$_2$)$_{n''''}$—Z''''

(wherein in the preceding formulas
Z'''' represents a polysiloxane residue, and
n'''' represents an integer in the range from 1 to 20); and
n is defined as above}, or
the following general formula (5'):

$$Z\text{—}(CH_2)_{\overline{n}}\text{—}\underset{OH}{\overset{|}{CH}}\text{—}CH_2\text{—}N\underset{R^5}{\overset{\diagup}{\diagdown}}\underset{N}{\overset{\diagup}{\diagdown}} \quad (5')$$

{wherein
Z is defined as above;
$R^5$ represents
—$CH_2$—$CH(NH_2)COOH$,
—$CH_2$—$CH(NH(\text{—}CH_2\text{—}CH(OH)\text{—}(CH_2)_{n'}\text{—}Z'))$ COOH, or
—$CH_2$—$CH(N(\text{—}CH_2\text{—}CH(OH)\text{—}(CH_2)_{n'}\text{—}Z')\text{—}CH_2\text{—}CH(OH)\text{—}(CH_2)_{n''}\text{—}Z'')COOH$
(wherein in the preceding formulas
Z' and Z" and n' and n" are defined as above); and
n is defined as above}.

The n, n', n", n''' and n'''' in the above-cited formulas (3'), (4') and (5') are each integers preferably in the range of 1 to 10 and more preferably 1 to 4 and even more preferably are 1 or 2 and particularly preferably are 1.

The organopolysiloxane residue is preferably represented by the following general formula (6):

$$(CH_3)_2Si\text{—}O\text{—}(\underset{CH_3}{\overset{R^1}{\overset{|}{Si}}}\text{—}O)_{\overline{x}}(\underset{CH_3}{\overset{D}{\overset{|}{Si}}}\text{—}O)_{\overline{y}}\underset{}{\overset{D}{\overset{|}{Si}}}(CH_3)_2 \quad (6)$$

{wherein
$R^1$ is defined as above;
D represents —$(CH_2)_a$—O—$(C_bH_{2b}O)_c$— (wherein a, b, and c are defined as above) or a group as defined for $R^1$ above, with the proviso that all of the D groups are not $R^1$; and
x and y are defined as above} or
by the following general formula (7):

$$\boxed{(\underset{CH_3}{\overset{R^1}{\overset{|}{Si}}}\text{—}O)_{\overline{r}}(\underset{CH_3}{\overset{D}{\overset{|}{Si}}}\text{—}O)_{\overline{s}}} \quad (7)$$

(wherein $R^1$, D, r, and s are defined as above and r+s represents an integer in the range from 3 to 20).

It is more preferable for the amino acid-modified organopolysiloxane (A) to have, in the molecule, at least one moiety represented by the following formula (3"), (4"), or (5"):

$$\text{—}(CH_2)_{\overline{a}}\text{—}O\text{—}(CH_2\text{—}\underset{CH_3}{\overset{|}{CHO}})_{\overline{d}}\text{—}(CH_2CH_2O)_{\overline{e}}\text{—}(CH_2)_{\overline{n}}\text{—}\underset{OH}{\overset{|}{CH}}\text{—}CH_2\text{—}\underset{H}{\overset{|}{N}}\text{—} \quad (3")$$

$$\text{—}(CH_2)_{\overline{a}}\text{—}O\text{—}(CH_2\text{—}\underset{CH_3}{\overset{|}{CHO}})_{\overline{d}}\text{—}(CH_2CH_2O)_{\overline{e}}\text{—}(CH_2)_{\overline{n}}\text{—}\underset{OH}{\overset{|}{CH}}\text{—}CH_2\text{—}\underset{H}{\overset{|}{N}}\text{—}N\diagdown \quad (4")$$

$$\text{—}(CH_2)_{\overline{a}}\text{—}O\text{—}(CH_2\text{—}\underset{CH_3}{\overset{|}{CHO}})_{\overline{d}}\text{—}(CH_2CH_2O)_{\overline{e}}\text{—}(CH_2)_{\overline{n}}\text{—}\underset{OH}{\overset{|}{CH}}\text{—}CH_2\text{—}\underset{H}{\overset{|}{N}}\text{—}N\diagdown \quad (5")$$

(n, a, d, and e in these formulas are defined as above).

Lysine, arginine, and histidine each have at least two reactive nitrogen atoms, as shown below by the arrows.

lysine    arginine    histidine

Accordingly, in those instances where the carboxy-unprotected amino acid (a) is a basic amino acid selected from the group consisting of lysine, arginine, and histidine, the amino acid-modified organopolysiloxane of the present invention is a mixture of basic amino acid-modified polysiloxanes that have in each molecule a moiety represented by the above-cited formula (3), (4), or (5) or the above-cited formula (3"), (4"), or (5"), or is a mixture of the basic amino acid-modified polysiloxanes represented by the above-cited general formula (1'), (2'), or (3'). These all share a structure in which a divalent moiety of —CH(OH)—$CH_2$—, which originates with the ring-opening reaction of the epoxy group, is bonded to a reactive nitrogen atom as cited above.

The basic amino acid under consideration is preferably arginine. Thus, arginine-modified organopolysiloxane is preferred for the amino acid-modified organopolysiloxane of the present invention.

This arginine-modified polysiloxane is preferably arginine-modified polysiloxane obtainable by the reaction of arginine with an organopolysiloxane that has an epoxy group and an ether chain in the molecule, and that is represented by the above-cited general formula (1'). The arginine-modified organopolysiloxane obtainable in this manner is a mixture of a plurality of arginine-modified polysiloxanes that have in the molecule a moiety represented by a formula (a, d, e, and n in these formulas are defined as above) selected from those given below.

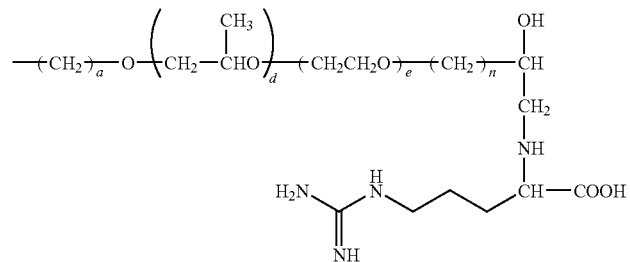
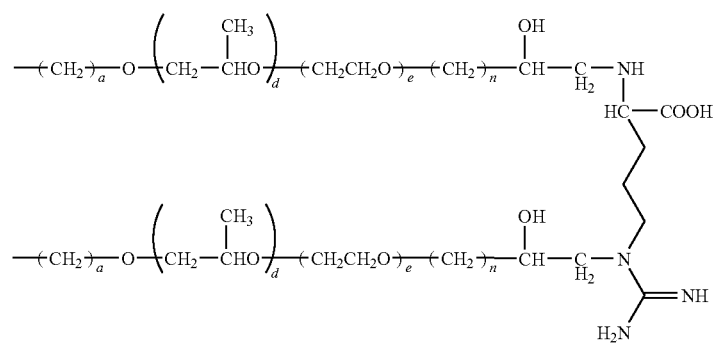
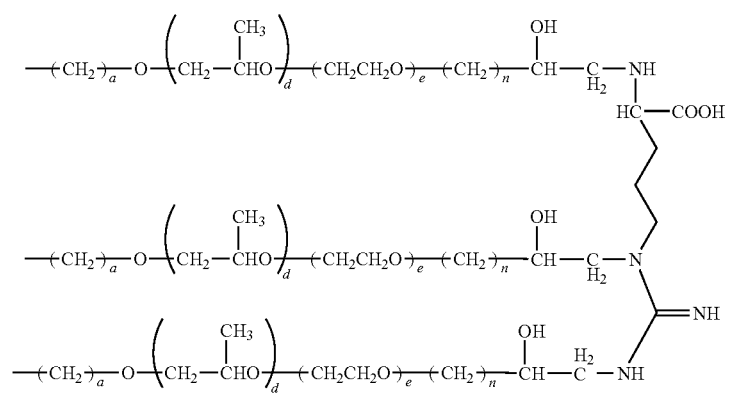
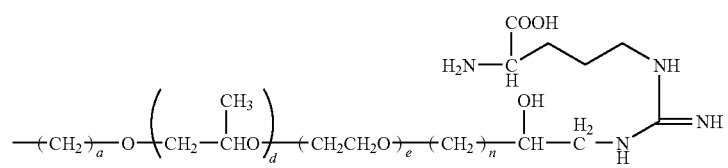
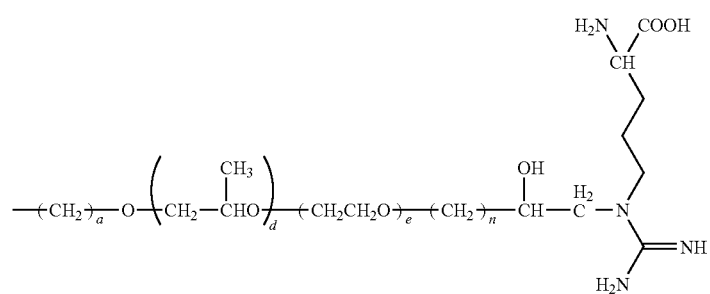

-continued

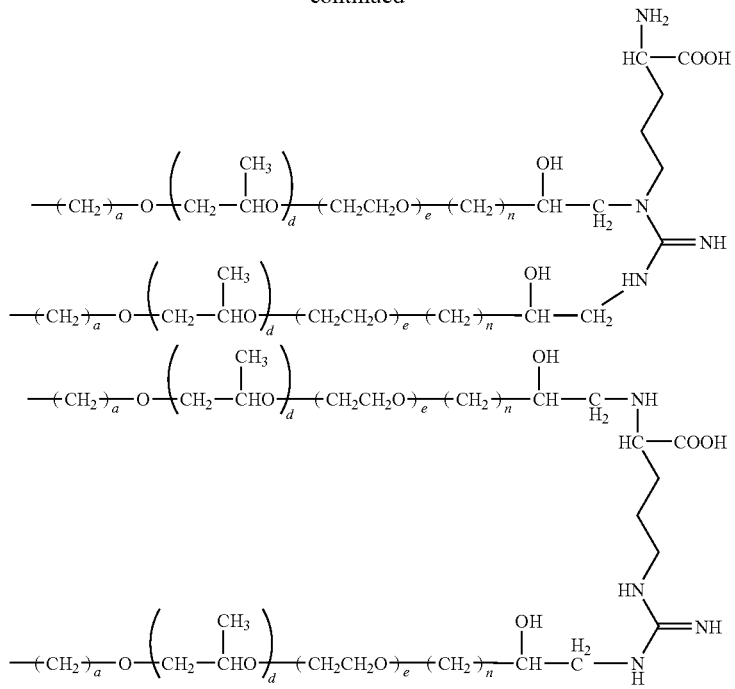

Arginine modified-polysiloxane having the moiety represented by the formula:

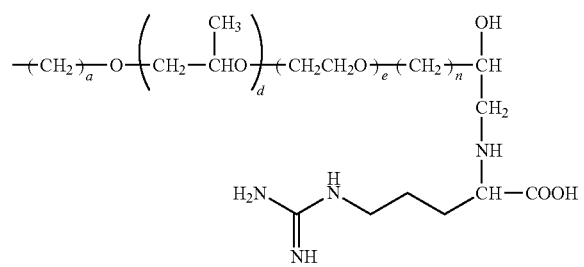

is particularly preferred among the arginine-modified polysiloxanes represented by the individual formulas given above. Accordingly, arginine-modified organopolysiloxane represented by the following general formula (9):

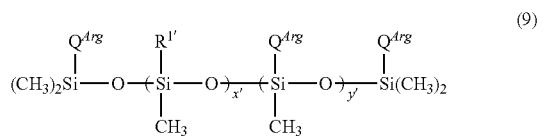

(9)

{wherein
R$^{1'}$ is defined as above;
Q$^{Arg}$ is a group represented by the following formula:

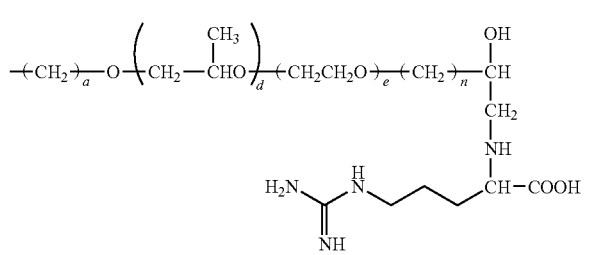

(wherein n, a, d, and e are defined as above), or represents a group as defined for R$^{1'}$ above, with the proviso that all of the Q$^{Arg}$ groups are not R$^{1'}$; and x' and y' are defined as above} is a particularly preferred amino acid-modified organopolysiloxane of the present invention.

The amino acid-modified organopolysiloxane emulsion of the present invention exhibits excellent conditioning effects (for example, improved hair combability and improved tactile sensation of hair), an excellent moisturizing effect, an excellent capacity to prevent static electrification, improved foaming properties, improved rinsing properties, improvement of the sticky sensation on the skin, and so forth, and is therefore useful as an ingredient for cosmetic products. Accordingly, the amino acid-modified organopolysiloxane emulsion of the present invention can be incorporated, as a beautifying component, into cosmetic products, in combination with other cosmetic ingredients that are typically used in cosmetic products.

The cosmetic ingredients that are typically used in cosmetic products can be exemplified by oils, hydrophilic media, humectants, silicones, ultraviolet protectants, water-soluble polymers, water-swellable clay minerals, preservatives, antimicrobial agents, physiologically active components, pH adjusters, organic solvents, oxidation inhibitors, chelating agents, fragrances, colorants, and so forth.

The origin of the oil is not critical as long as the oil is hydrophobic, and the oil may be a solid, semisolid, or liquid and may be nonvolatile, semi-volatile, or volatile. The oil can be specifically exemplified by silicone oils, hydrocarbon oils and waxes, plant and animal oils, higher alcohols, ester oils, and so forth. Silicone oils are preferred because they can provide a refreshing sensation upon use. A single oil may be used, or two or more may be used in combination. The oil content in the cosmetic product is preferably 1 to 50 mass % of the total mass of the cosmetic product.

The molecular structure of the silicone oil may be cyclic, linear, or branched. Its viscosity at 25° C. is generally in the range from 0.65 to 100,000 mm²/s and is preferably in the range from 0.65 to 10,000 mm²/s. Cyclic silicone oils can be specifically exemplified by hexamethylcyclotrisiloxane (D3), octamethylcyclotetrasiloxane (D4), decamethylcyclopentasiloxane (D5), dodecamethylcyclohexasiloxane (D6), 1,1-diethylhexamethylcyclotetrasiloxane, phenylheptamethylcyclotetrasiloxane, 1,1-diphenylhexamethylcyclotetrasiloxane, 1,3,5,7-tetravinyltetramethylcyclotetrasiloxane, 1,3,5,7-tetramethylcyclotetrasiloxane, 1,3,5,7-tetracyclohexyltetramethylcyclotetrasiloxane, tris(3,3,3-trifluoropropyl)trimethylcyclotrisiloxane, 1,3,5,7-tetra(3-aminopropyl)tetramethylcyclotetrasiloxane, 1,3,5,7-tetra(N-(2-aminoethyl)-3-aminopropyl)tetramethylcyclotetrasiloxane, 1,3,5,7-tetra(3-mercaptopropyl)tetramethylcyclotetrasiloxane, 1,3,5,7-tetra(3-glycidoxypropyl)tetramethylcyclotetrasiloxane, 1,3,5,7-tetra(3-methacryloxypropyl)tetramethylcyclotetrasiloxane, 1,3,5,7-tetra(3-acryloxypropyl)tetramethylcyclotetrasiloxane, 1,3,5,7-tetra(3-carboxypropyl)tetramethylcyclotetrasiloxane, 1,3,5,7-tetra(3-vinyloxypropyl)tetramethylcyclotetrasiloxane, 1,3,5,7-tetra(p-vinylphenyl)tetramethylcyclotetrasiloxane, 1,3,5,7-tetra[3-(p-vinylphenyl)propyl]tetramethylcyclotetrasiloxane, 1,3,5,7-tetra[3-(p-isopropenylbenzoylamino)propyl]tetramethylcyclotetrasiloxane, 1,3,5,7-tetra(N-methacryloyl-N-methyl-3-aminopropyl)tetramethylcyclotetrasiloxane, 1,3,5,7-tetra(N-lauroyl-N-methyl-3-aminopropyl)tetramethylcyclotetrasiloxane, 1,3,5,7-tetra(N-acryloyl-N-methyl-3-aminopropyl)tetramethylcyclotetrasiloxane, 1,3,5,7-tetra(N,N-bis(methacryloyl)-3-aminopropyl)tetramethylcyclotetrasiloxane, 1,3,5,7-tetra(N,N-bis(lauroyl)-3-aminopropyl)tetramethylcyclotetrasiloxane, and so forth. The linear silicone oils can be exemplified by dimethylpolysiloxane having both ends of the molecular chain blocked by trimethylsiloxy groups, methylphenylpolysiloxane having both ends of the molecular chain blocked by trimethylsiloxy groups, dimethylsiloxane-methylphenylsiloxane copolymer having both ends of the molecular chain blocked by trimethylsiloxy groups, dimethylsiloxane-methyl (3,3,3-trifluoropropyl)siloxane copolymer having both ends of the molecular chain blocked by trimethylsiloxy groups, α,ω-dihydroxypolydimethylsiloxane, α,ω-dimethoxypolydimethylsiloxane, tetramethyl-1,3-dihydroxydisiloxane, octamethyl-1,7-dihydroxytetrasiloxane, hexamethyl-1,5-diethoxytrisiloxane, hexamethyldisiloxane, octamethyltrisiloxane, and so forth. The branched silicone oils are exemplified by methyltristrimethylsiloxysilane, ethyltristrimethylsiloxysilane, propyltristrimethylsiloxysilane, tetrakistrimethylsiloxanesilane, and phenyltristrimethylsiloxysilane. Volatile species are preferred, and two or more of these may be used in combination.

The hydrocarbon oils and waxes are exemplified by ozokerite, squalane, squalene, ceresin, paraffin, paraffin wax, liquid paraffin, pristane, polyisobutylene, polybutene, microcrystalline wax, vaseline, and so forth. Two or more of these may be used in combination.

The plant and animal oils are exemplified by avocado oil, linseed oil, almond oil, ibota wax, perilla oil, olive oil, cacao butter, kapok tree wax, kaya oil, carnauba wax, cod liver oil, candelilla wax, beef tallow, hoof oil, cow bone fat, hardened beef tallow, apricot kernel oil, spermaceti wax, hardened oils, wheat germ oil, sesame oil, rice germ oil, rice bran oil, sugarcane wax, camellia kissi seed oil, safflower oil, shea butter, Paulownia oil, cinnamon oil, jojoba wax, shellac wax, turtle oil, soy oil, tea seed oil, camellia oil, evening primrose oil, corn oil, lard, rapeseed oil, Japanese tung oil, bran wax, germ oil, horse fat, persic oil, palm oil, palm kernel oil, castor oil, hardened castor oil, castor oil fatty acid methyl ester, sunflower oil, grape seed oil, bayberry wax, jojoba oil, macadamia nut oil, beeswax, mink oil, cottonseed oil, cotton wax, Japan tallow, sumac kernel oil, montan wax, palm oil, hardened palm oil, cocotriglycerides, mutton tallow, peanut oil, lanolin, liquid lanolin, reduced lanolin, lanolin alcohol, hardened lanolin, lanolin acetate, lanolin fatty acid isopropyl ester, hexyl laurate, POE lanolin alcohol ether, POE lanolin alcohol acetate, lanolin fatty acid polyethylene glycol, POE hydrogenated lanolin alcohol ether, egg yolk oil, and so forth. These may be used in combinations of two or more.

The higher alcohols are exemplified by lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecynol, cholesterol, phytosterols, POE cholesterol ether, monostearyl glycerol ether (batyl alcohol), monooleyl glyceryl ether (selachyl alcohol), and so forth. These may be used in combinations of two or more.

The ester oils are exemplified by diisobutyl adipate, 2-hexyldecyl adipate, di-2-heptylundecyl adipate, N-alkylglycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, isononyl isononanoate, neopentyl glycol dicaprate, triethyl citrate, 2-ethylhexyl succinate, amyl acetate, ethyl acetate, butyl acetate, isocetyl stearate, butyl stearate, diisopropyl sebacate, 2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, 2-ethylhexyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, diisostearyl malate, and so forth, and the glyceride oils are exemplified by acetoglyceryl, glyceryl triisooctanoate, glyceryl triisostearate, glyceryl triisopalmitate, glyceryl tri(caprylate.caprate), glyceryl monostearate, glyceryl di-2-heptylundecanoate, glyceryl trimyristate, diglyceryl myristate isostearate, and so forth. These may be used in combinations of two or more.

The hydrophilic media are exemplified by monohydric lower alcohols such as ethanol, n-propanol, isopropanol, n-butanol, and so forth; dihydric alcohols such as 1,3-butylene glycol, ethylene glycol, propylene glycol, and so forth; polyalkylene glycols such as polyethylene glycol, dipropylene glycol, polypropylene glycol, and so forth; and polyhydric alcohols such as glycerol, diglycerol, trimethylolpropane, pentaerythritol, sorbitol, and so forth. Two or more of these can be used in combination. The content of the hydrophilic medium in the cosmetic product is preferably from 1 to 80 mass % of the total mass of the cosmetic product.

The humectant can be exemplified by glucose, xylitol, maltitol, hyaluronic acid, chondroitin sulfate, pyrrolidonecarboxylate salts, polyoxyethylene methylglucoside, polyoxypropylene methylglucoside, and so forth. Two or more of these can be used in combination. In some cases, a hydrophilic medium such as 1,3-butylene glycol, ethylene glycol, polyethylene glycol, propylene glycol, dipropylene glycol, polypropylene glycol, glycerol, diglycerol, trimethylolpropane, pentaerythritol, sorbitol, and the like, may also provide a cosmetic product with an improved moisturizing sensation.

The content of the humectant in the cosmetic product is preferably 0.1 to 30 mass % of the total mass of the cosmetic product.

The silicones can be exemplified by silicone gums, silicone resins, and silicone elastomer powders. Two or more of these may be used in combination.

The silicone gum is a straight-chain diorganopolysiloxane that has an extremely high degree of polymerization and is known as a silicone gum or organopolysiloxane gum. A typical example is represented by $(CH_3)_3SiO\{(CH_3)_2SiO\}_f\{(CH_3)R^7SiO\}_gSi(CH_3)_3$ (wherein $R^7$ is selected from vinyl, phenyl, $C_{6-20}$ alkyl, $C_{3-15}$ aminoalkyl, $C_{3-15}$ perfluoroalkyl, and $C_{3-15}$ quaternary ammonium salt group-containing alkyl, f=3000 to 6000, g=0 to 1000, f+g=3000 to 6000). Two or more of these may be used in combination.

The silicone resin is an organopolysiloxane with a highly branched structure, a net-like structure, or a cage-like structure and is a liquid or solid at ambient temperature. The solid silicone resins are exemplified by MQ resins, MDQ resins, MTQ resins, MDTQ resins, TD resins, TQ resins, and TDQ resins, which comprise arbitrary combinations of the triorganosiloxy unit (M unit) (wherein the organic group is only methyl, or is a combination of methyl with vinyl or phenyl), the diorganosiloxy unit (D unit) (wherein the organic group is only methyl, or is a combination of methyl with vinyl or phenyl), the monoorganosiloxy unit (T unit) (wherein the organic group is methyl, vinyl, or phenyl), and the siloxane unit (Q unit). Other examples are trimethylsiloxysilicic acid, polyalkylsiloxysilicic acid, trimethylsiloxysilicic acid containing the dimethylsiloxy unit, alkyl(perfluoroalkyl)siloxysilicic acid, and so forth. The aforementioned silicone resins are preferably oil soluble and particularly preferably are soluble in octamethyltetrasiloxane (D4) and/or decamethylcyclopentasiloxane (D5). Two or more of these may be used in combination.

The silicone gum and silicone resin may be directly incorporated into a cosmetic product or can also be incorporated after being dissolved in a volatile or nonvolatile silicone oil or dissolved in a volatile or nonvolatile hydrocarbon oil. The content of the silicone gum and silicone resin is preferably 0.1 to 20 mass % and more preferably 1 to 10 mass % of the total quantity of the cosmetic product. 50 to 500 weight parts of silicone gum or silicone resin per 100 weight parts of the cosmetic product is preferred for obtaining a cosmetic product which adheres more tightly to the skin.

The silicone elastomer powder is mainly a crosslinked product of a straight-chain diorganopolysiloxane and may have various shapes, such as spherical, flattened, irregular, and so forth. It is preferable to use a silicone elastomer having a particulate shape, in particular a silicone elastomer powder in which the primary particles are spherical wherein the mean primary particle size measured by laser diffraction/scattering and/or the primary particle size obtained by electron microscopic observation is in the range from 0.1 to 50 μm. In addition, the silicone elastomer constituting the silicone elastomer powder has a Type A durometer hardness of preferably no more than 80 and more preferably no more than 65 according to JIS K 6253, "Rubber, vulcanized or thermoplastic—Determination of hardness". Two or more silicone elastomer powders may be used in combination.

The silicone elastomer powder can be prepared, for example, by curing a composition, residing in an emulsified state or sprayed state, comprising diorganopolysiloxane bearing at least two alkenyl groups, alkylhydrogenpolysiloxane bearing at least two silicon-bonded hydrogen atoms, and chloroplatinic acid. The alkenyl-functional diorganopolysiloxane can be exemplified by dimethylpolysiloxane having both molecular terminals capped with dimethylvinylsiloxy groups, but this may also be an organic compound having two or more vinyl and/or allyl groups in the molecule, such as α,ω-alkenyldiene, glycerol triallyl ether, polyoxyalkynylated glycerol triallyl ether, trimethylolpropane triallyl ether, polyoxyalkynylated trimethylolpropane triallyl ether, and so forth.

Silicone elastomer powders are described, for example, in JP 02-243612 A, JP 08-012545 A, JP 08-012546 A, JP 08-012524 A, JP 09-241511 A, JP 10-036219 A, JP 11-193331 A, JP 2000-281523 A, and so forth. Within the sphere of commercial products, Dow Corning Toray Co., Ltd., offers the Trefil E series, e.g., Trefil E-505, E-506, E-507, E-508, EP-9215, EP9515, EP-9289, EP-9293, EP-9261 and Dow Corning 9701 and so forth, which correspond to the crosslinked silicone powders listed in the "Japanese Cosmetic Ingredients Codex". These silicone elastomer powders may be subjected to a surface treatment. Examples of the surface treatment agent include methylhydrogenpolysiloxane; silicone resins; metal soaps; silane coupling agents; inorganic oxides such as silica, titanium oxide, and so forth; and fluorocompounds such as perfluoroalkylsilanes, perfluoroalkyl phosphate ester salts, and so forth.

The silicone elastomer powder is preferably incorporated into the cosmetic product as a paste (blended with an oil component) or a water-based dispersion. More specific examples are a paste prepared by mixing silicone elastomer powder with an oil that is liquid at ambient temperature and selected from ester oils, hydrocarbon oils, higher alcohols, and plant and animal oils; and a dispersion of silicone elastomer powder dispersed by mechanical force in water containing an emulsifying agent.

Silicone elastomer powders also often have a particle size exceeding 10 μm and have been difficult to incorporate into aqueous compositions in a stable manner, but can be incorporated in a stable manner by combined use with the amino acid-modified organopolysiloxane emulsion of the present invention. The organopolysiloxane elastomer powder content in a cosmetic product is preferably 0.1 to 30 mass % of the total mass of the cosmetic product.

A silicone-modified organic polymer may be incorporated as a silicone. Silicone-modified organic polymers can be exemplified by polydimethylsiloxane graft-type acrylic copolymers, the carboxysiloxane dendrimer graft-type acrylic copolymer disclosed in JP 2000-063225 A, and the acrylic copolymer containing a fluorinated organic group and a carboxysiloxane dendrimer structure as disclosed in JP 2003-226611 A. Two or more of these may be used in combination.

The UV protectant may an inorganic or organic UV screening agent. The inorganic UV screening agents are typically inorganic powders, for example, a metal oxide such as titanium oxide, zinc oxide, cerium oxide, titanium suboxide, iron-doped titanium oxide, and so forth; a metal hydroxide such as iron hydroxide and so forth; metal flakes such as iron oxide flakes, aluminum flakes, and so forth; or a ceramic such as silicon carbide and so forth. Particularly preferred among these is at least one selection from microparticulate metal oxides or microparticulate metal hydroxides having a mean particle size in the range from 1 to 100 nm. Two or more of these may be used in combination. These powders are preferably subjected to a known surface-treatment, for example, treatment with a fluorine compound (treatment with perfluoroalkyl phosphate and preferably treatment with perfluoroalkylsilane, perfluoropolyether, fluorosilicone, or fluorinated silicone resin), silicone treatment (methylhydrogenpolysiloxane treatment, dimethylpolysiloxane treatment, and vapor-phase tetramethyltetrahydrogencyclotetrasiloxane treatment are preferred), treatment with silicone resin (treatment with trimethylsiloxysilicic acid is preferred), pendant treatment (a method in which, for example, an alkyl chain is added after a vapor-phase silicone treatment), treatment with a silane coupling agent, treatment with a titanate coupling agent, treatment with a silane (alkylsilane treatment and alkylsilazane treatment are preferred), treatment with an oil, treatment with N-acylated lysine, treatment with polyacrylic acid, metal soap treatment (stearate and/or myristate are preferred), treatment with acrylic resin, treatment with metal oxide, and so forth. Treatment with a plurality of these treatments is preferred. For example, the surface of a microparticulate titanium oxide may be coated with metal oxide such as silicon oxide and alumina, followed by treatment of the surface with alkylsilane. The total amount of surface treatment is preferably in the range from 0.1 to 50 mass % with reference to the powder.

The organic UV screening agent is exemplified by salicylic acid types such as homomenthyl salicylate, octyl salicylate, triethanolamine salicylate, and so forth; PABA types such as para-aminobenzoic acid, ethyldihydroxypropyl para-aminobenzoate, glyceryl para-aminobenzoate, octyl dimethyl para-aminobenzoate, amyl para-dimethylaminobenzoate, 2-ethylhexyl para-dimethylaminobenzoate, and so forth; benzophenones such as 4-(2-(β-glucopyranosyloxy)propoxy-2-hydroxybenzophenone, dihydroxydimethoxybenzophenone, sodium dihydroxydimethoxybenzophenonedisulfonate, 2-hydroxy-4-methoxybenzophenone, hydroxymethoxybenzophenonesulfonic acid and its trihydrate, sodium hydroxymethoxybenzophenonesulfonate, 2-hydroxy-4-methoxybenzophenone-5-sulfuric acid, 2,2'-dihydroxy-4-methoxybenzophenone, 2,4-dihydroxybenzophenone, 2,2',4,4'-tetrahydroxybenzophenone, 2,2'-dihydroxy-4,4'-dimethoxybenzophenone, 2-hydroxy-4-N-octoxybenzophenone, and so forth; cinnamic acids such as 2-ethylhexyl para-methoxycinnamate (also called octyl para-methoxycinnamate), glyceryl di-para methoxycinnamate mono-2-ethylhexanoate, methyl 2,5-diisopropylcinnamate, 2,4,6-tris[4-(2-ethylhexyloxycarbonyl)anilino]-1,3,5-triazine, methylbis(trimethylsiloxy)silylisopentyl trimethoxycinnamate, isopropyl para-methoxycinnamate/diisopropylcinnamic acid ester mixture, p-methoxyhydrocinnamic acid diethanolamine salt, and so forth; benzoylmethanes such as 2-phenylbenzimidazole-5-sulfuric acid, 4-isopropyldibenzoylmethane, 4-tert-butyl-4'-methoxydibenzoylmethane, and so forth; and also 2-cyano-3,3-diphenylprop-2-enoic acid 2-ethylhexyl ester (also called octocrylene), 2-ethylhexyl dimethoxybenzylidenedioxoimidazolidinepropionate, 1-(3,4-dimethoxyphenyl)-4,4-dimethyl-1,3-pentanedione, cinoxate, methyl o-aminobenzoate, 2-ethylhexyl 2-cyano-3,3-diphenylacrylate, 3-(4-methylbenzylidene)camphor, octyltriazone, 2-ethylhexyl 4-(3,4-dimethoxyphenylmethylene)-2,5-dioxo-1-imidazolidinepropionate, polymeric derivatives of the preceding, and silane derivatives thereof. Two or more of these may be used in combination.

The organic UV screening agent may be used dispersed in a polymer powder. The polymer powder may be hollow or solid, has a mean primary particle size preferably in the range from 0.1 to 50 μm, and has a broad or sharp particle size distribution. The type of polymer can be exemplified by acrylic resins, methacrylic resins, styrene resins, polyurethane resins, polyethylene, polypropylene, polyethylene terephthalate, silicone resins, nylons, acrylamide resins, and so forth. A polymer powder containing an organic UV screening agent in the range from 0.1 to 30 mass % is preferred, and polymer powder containing the UV-absorber 4-tert-butyl-4'-methoxydibenzoylmethane is particularly preferred.

At least one selection from the group consisting of microparticulate titanium oxide, microparticulate zinc oxide, 2-ethylhexyl para-methoxycinnamate, 4-tert-butyl-4'-methoxydibenzoylmethane, and benzophenone-type UV absorbers is very suitably used as the UV protectant since these are commonly used, easy to obtain, and have an excellent UV protective effect. The use of inorganic and organic UV screening agents in combination is particularly preferred, and the use of a UV screening agent directed against UV-A in combination with a UV screening agent directed against UV-B is even more preferred. The content of the UV protectant in the cosmetic product, considered in terms of the total of the inorganic and/or organic UV screening agent, is preferably in the range of 0.1 to 60 mass % of the cosmetic product and more preferably is in the range of 3 to 40 mass %. Moreover, the inorganic UV screening agent content is preferably in the range of 0.1 to 30 mass % of the cosmetic product, and the organic UV screening agent content is preferably in the range of 0.1 to 20 mass % of the cosmetic product.

The water-soluble polymer can be exemplified by amphoteric, cationic, anionic, and nonionic water-soluble polymers. Two or more of these may be used in combination.

The amphoteric water-soluble polymer can be exemplified by amphoteric starch, dimethyldiallylammonium chloride derivatives (e.g., copolymers of acrylamide, acrylic acid, and dimethyldiallylammonium chloride, copolymers of acrylic acid and dimethyldiallylammonium chloride), and methacrylic acid derivatives (e.g., polymethacryloylethyldimethylbetaine, copolymers of alkyl methacrylate and N-methacryloyloxyethyl-N,N-dimethylammonium-α-methylcarboxybetaine, and so forth). Two or more of these may be used in combination.

The cationic water-soluble polymer can be exemplified by quaternary nitrogen-modified polysaccharides (e.g., cation-modified cellulose, cation-modified hydroxyethyl cellulose, cation-modified guar gum, cation-modified locust bean gum, cation-modified starch, and so forth), dimethyldiallylammonium chloride derivatives (e.g., copolymers of dimethyldiallylammonium chloride and acrylamide, polydimethylmethylenepiperidinium chloride, and so forth), vinylpyrrolidone derivatives (e.g., the salts of vinylpyrrolidone/dimethylaminoethyl methacrylate copolymers, copolymers of vinylpyrrolidone and methacrylamidopropyltrimethylammonium chloride, copolymers of vinylpyrrolidone and methylvinylimidazolium chloride, and so forth), and methacrylic acid derivatives (e.g., copolymers of methacryloylethyldimethylbetaine, methacryloylethyltrimethylammonium chloride, and 2-hydroxyethyl methacrylate; copolymers of methacryloylethyldimethylbetaine, methacryloylethyltrimethylammonium chloride, and methoxypolyethylene glycol methacrylate; and so forth). Two or more of these may be used in combination.

The anionic water-soluble polymer can be exemplified by polyacrylic acid and its alkali metal salts, polymethacrylic acid and its alkali metal salts, hyaluronic acid and its alkali metal salts, acetylated hyaluronic acid and its alkali metal salts, water-soluble polymers of aliphatic carboxylic acids (e.g., the hydrolyzates of methyl vinyl ether-maleic anhydride copolymers, and so forth) and their metal salts, carboxymethyl cellulose and its alkali metal salts, copolymers of methyl vinyl ether and a maleic acid hemi-ester, acrylic resin alkanolamine solutions, and carboxyvinyl polymers. Two or more of these may be used in combination.

The nonionic water-soluble polymer can be exemplified by polyvinylpyrrolidone, highly polymerized polyethylene glycol, vinylpyrrolidone/vinyl acetate copolymers, vinylpyrrolidone/dimethylaminoethyl methacrylate copolymers, vinyl caprolactam/vinylpyrrolidone/dimethylaminoethyl methacrylate copolymers, cellulose and its derivatives (e.g., methyl cellulose, ethyl cellulose, hydroxyethyl cellulose, hydroxypropyl cellulose, and carboxymethyl cellulose), and natural polymer compounds such as keratin and collagen and their derivatives, calcium alginate, pullulan, agar, gelatin, tamarind seed polysaccharides, xanthan gum, carrageenan, high-methoxyl pectin, low-methoxyl pectin, guar gum, pectin, gum arabic, crystalline cellulose, arabinogalactan, gum karaya, tragacanth gum, alginic acid, albumin, casein, curdlan, gellan gum, dextran, quince seed gum, traganth gum, chitin and chitosan derivatives, starches (rice, corn, potato, wheat, and so forth), and so forth. Two or more of these may be used in combination.

The water-soluble polymer is preferably mixed with other ingredients of a cosmetic product after the water-soluble polymer has been made into a uniform aqueous solution or dispersion by dissolution or dispersion in water. The water-soluble polymer content in a cosmetic product is preferably in the range of 0.001 to 5 mass % of the cosmetic product and is more preferably in the range of 0.01 to 3 mass % of the cosmetic product. A satisfactory thickening effect cannot be expected at a content below 0.001 mass %, while exceeding 5 mass % results in an excessively high viscosity for the cosmetic product upon incorporation of the water-soluble polymer and can lead to a poor use sensation.

The water-swellable clay mineral is a type of colloid-containing aluminum silicate having a three-layer structure, and can be exemplified by the following formula:

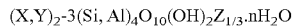

(wherein X is Al, Fe(III), Mn(III), or Cr(III); Y is Mg, Fe(II), Ni, Zn, or Li; and Z is K, Na, or Ca). Such water-swellable clay minerals are specifically exemplified by bentonite, montmorillonite, beidellite, nontronite, saponite, hectorite, and magnesium aluminum silicate, and these may be either natural or synthetic material. Two or more of these can be used in combination.

The water-swellable clay mineral is preferably mixed with other ingredients of a cosmetic product after the water-swellable clay mineral has been made into a uniform aqueous solution or dispersion by dissolution or dispersion in water. The content of the water-swellable clay mineral in a cosmetic product is preferably in the range of 0.001 to 5 mass % of the cosmetic product and more preferably in the range of 0.01 to 3 mass % of the cosmetic product.

A satisfactory thickening effect cannot be expected at a content below 0.001 mass %, while exceeding 5 mass % results in an excessively high viscosity for the cosmetic product upon incorporation of the water-swellable clay mineral and can lead to a poor use sensation.

The preservative can be exemplified by the alkyl esters of para-hydroxybenzoic acid, benzoic acid, sodium benzoate, sorbic acid, potassium sorbate, phenoxyethanol, and so forth. Two or more of these can be used in combination. The silicone content in the cosmetic product is preferably 0.1 to 5 mass % of the total mass of the cosmetic product.

The antimicrobial agent can be exemplified by benzoic acid, salicylic acid, carbolic acid, sorbic acid, the alkyl esters of para-hydroxybenzoic acid, para-chloro-meta-cresol, hexachlorophene, benzalkonium chloride, chlorhexidine chloride, trichlorocarbanilide, trichlosan, light-sensitive ingredients, phenoxyethanol, methylisothiazolinone, and so forth. Two or more of these can be used in combination. The silicone content in the cosmetic product is preferably 0.1 to 5 mass % of the total mass of the cosmetic product.

The physiologically active component can be exemplified by antiinflammatory agents, aging inhibitors, tightening agents, hair growth stimulants, hair restoration agents, blood circulation promoters, desiccants, algefacients, calorifacients, vitamins, amino acids, wound healing promoters, soothing agents, analgesics, cell activators, enzymatic components, and so forth. Particularly preferred among the preceding are physiologically active components comprising natural plant extract components, seaweed extract components, and herbal and natural medicines. The incorporation of one or two or more of these physiologically active components in the cosmetic product is preferred. The content of the physiologically active component in the cosmetic product is preferably 0.1 to 10 mass % of the total mass of the cosmetic product.

Specific examples are *Angelica keiskei* extract, avocado extract, *Hydrangea serrata* extract, *Althea* extract, *Arnica* extract, aloe extract, apricot extract, apricot kernel extract, *Gingko biloba* extract, fennel fruit extract, turmeric root extract, oolong tea extract, *Rosa multiflora* extract, *Echinacea angustifolia* leaf extract, *Scutellaria baicalensis* root extract, *Phellodendron amurense* extract, *Coptis rhizome* extract, *Hordeum vulgare* seed extract, *Hypericum perforatum* extract, *Lamium album* extract, *Nasturtium officinale* extract, orange extract, dried sea water, seaweed extract, hydrolyzed elastin, hydrolyzed wheat flour, hydrolyzed silk, Chamomile extract, carrot extract, *Artemisia capillaris* flower extract, licorice extract, *karkade* extract, *Pyracantha fortuneana* extract, kiwi extract, *Cinchona* extract, cucumber extract, guanosine, *Gardenia florida* extact, *Sasa veitchii* extract, *Sophora angustifolia* extract, walnut extract, grapefruit extract, *Clematis vitalba* leaf extract, chlorella extract, *Morus alba* root extract, *Gentiana lutea* extract, black tea extract, yeast extract, burdock extract, fermented rice bran extract, rice germ oil, comfrey extract, collagen, *Vaccinum vitis idaea* extract, *Asiasarum* root extract, *Bupleurum falcatum* extract, umbilical extract, pomegranate extract, *Salvia* extract, soapwort extract, Sasa bamboo grass extract, *Crataegus cuneata* fruit extract, *Zanthoxylum piperitum* extract, *shiitake* extract, *Rehmannia* root extract, *Lithospermum erythrorhizone* root extract, *Perilla ocymoides* extract, *Tilia cordata* flower extract, *Spiraea ulmaria* extract, *Paeonia albiflora* extract, *Acorus calamus* root extract, *Betula alba* extract, *Equisetum arvense* extract, *Hedera* helix extract, *Crataegus oxyacantha* extract, *Sambucus nigra* extract, *Achillea millefolium* extract, *Mentha piperita* leaf extract, sage extract, *Malva sylvestris* extract, *Cnidium officinale* root extract, *Swertia japonica* extract, soybean extract, *Zizyphus jujuba* fruit extract, thyme extract, tea extract, *Eugenia caryophyllus* flower extract, *Imperata cylindrica* extract, *Citrus unshiu* Marc extract, *Angelica* root extract, *Calendula officinalis* extract, *Prunus persica* stone extract, *Citrus aurantium* peel extract, *Houttuynia cordata* extract, tomato extract, natto extract, carrot extract, garlic extract, Rosa canina fruit extract, *Hibiscus* extract, *Ophiopogon* extract, *Nelumbo nucifera* extract, parsley extract, honey, witch hazel extract, *Parietaria officinalis* extract, *Isodon trichocarpus* extract, bisabolol, *Eriobotrya japonica* extract, coltsfoot flower extract, *Petasites japonicus* extract, *Poria cocos* extract, butcher's broom extract, grape extract, propolis, *Luffa cylindrica* fruit extract, safflower flower extract, peppermint extract, *Tillia miquellana* extract, *Paeonia suffruticosa* root extract, hops extract, *Pinus sylvestris* cone extract, horse chestnut extract, Japanese skunk cabbage extract, *Sapindus mukurossi* peel extract, *Melissa* extract, peach extract, *Centaurea cyanus* flower extract,

*Eucalyptus* extract, *Saxifraga sarementosa* extract, *Citrus junos* extract, *Coix* seed extract, *Artemisia princeps* extract, lavender extract, apple extract, lettuce extract, lemon extract, *Astragalus sinicus* extract, rose extract, rosemary extract, Roman chamomile extract, royal jelly extract, and so forth.

Other examples are biopolymers such as deoxyribonucleic acid, mucopolysaccharides, sodium hyaluronate, sodium chondroitin sulfate, collagen, elastin, chitin, chitosan, hydrolyzed eggshell membrane, and so forth; amino acids such as glycine, valine, leucine, isoleucine, serine, threonine, phenylalanine, arginine, lysine, aspartic acid, glutamate, cystine, cysteine, methionine, tryptophan, and so forth; hormones such as estradiol, ethenylestradiol, and so forth; oil components such as sphingolipids, ceramides, cholesterol, cholesterol derivatives, phospholipids, and so forth; antiinflammatories such as ε-aminocaproic acid, glycyrrhizic acid, β-glycyrrhetinic acid, lysozyme chloride, guaiazulene, hydrocortisone, allantoin, tranexamic acid, azulene, and so forth; vitamins such as vitamins A, B2, B6, C, D, and E, calcium pantothenate, biotin, nicotinamide, vitamin C ester, and so forth; active components such as allantoin, diisopropylamine dichloroacetate, 4-aminomethyl cyclohexanecarboxylic acid, and so forth; cell activators such as α-hydroxy acids, β-hydroxy acids, and so forth; circulation promoters such as γ-oryzanol, vitamin E, and so forth; wound healing agents such as retinol, retinol derivatives, and so forth; algafacients such as cepharanthine, licorice extract, cayenne tincture, hinokitiol, iodized garlic extract, pyridoxine hydrochloride, dl-α-tocopherol, dl-α-tocopherol acetate, nicotinic acid, nicotinic acid derivatives, calcium pantothenate, D-pantothenyl alcohol, acetyl pantothenyl ethyl ether, biotin, allantoin, isopropyl methyl phenol, estradiol, ethynylestradiol, capronium chloride, benzalkonium chloride, diphenhydramine hydrochloride, Takanal™, salicylic acid, nonylic acid vanillylamide, nonanoic acid vanillylamide, Piroctone olamine, glyceryl pentadecanoate, 1-menthol, camphor, and so forth; and hair restoration agents such as mononitroguaiacol, resorcinol, γ-aminobutyric acid, benzethonium chloride, mexiletine hydrochloride, auxin, female hormones, cantharis tincture, cyclosporine, zinc pyrithione, hydrocortisone, minoxidil, polyoxyethylene sorbitan monostearate, peppermint oil, sasanishiki extract, and so forth.

The pH adjuster can be exemplified by lactic acid, citric acid, glycolic acid, succinic acid, tartaric acid, dl-malic acid, potassium carbonate, sodium bicarbonate, ammonium bicarbonate, and so forth. Two or more of these can be used in combination. The content of the pH adjuster in the cosmetic product is preferably 0.1 to 5 mass % of the total mass of the cosmetic product.

The organic solvent is, for example, an ether, while examples of propellants include LPG, N-methylpyrrolidone, and next-generation chlorofluorocarbons. Two or more of these can be used in combination. The content of the organic solvent in the cosmetic product is preferably 0.1 to 50 mass % of the total mass of the cosmetic product.

The oxidation inhibitor (antioxidant) can be exemplified by tocopherol, butylhydroxyanisole, dibutylhydroxytoluene, phytic acid, carotenoids, flavonoids, tannins, lignans, and saponins. Two or more of these may be used in combination. The oxidation inhibitor content in the cosmetic product is preferably 0.1 to 5 mass % of the total mass of the cosmetic product.

The chelating agent can be exemplified by EDTA, alanine, sodium edetate, sodium polyphosphate, sodium metaphosphate, and phosphoric acid. Two or more of these may be used in combination. The chelating agent content in the cosmetic product is preferably 0.1 to 5 mass % of the total mass of the cosmetic product.

The fragrance can be exemplified by fragrances extracted from the flowers, seeds, leaves, roots, and so forth, of various plants, including the various extracts provided as examples of the physiologically active component; fragrances extracted from seaweed; fragrances extracted from various parts or secretory glands of animals (e.g., musk and sperm oil); and artificially synthesized fragrances (e.g., menthol, musk, ethyl acetate, and vanilla). Two or more of these may be used in combination. The content of the fragrance in the cosmetic product is preferably 0.1 to 5 mass % of the total mass of the cosmetic product.

The colorant can be exemplified by dyes, pigments, and fluorescent whitening agents; the dyes include water-soluble dyes, oil-soluble dyes, natural dyes, synthetic dyes, and so forth; the pigments include extender pigments, inorganic pigments, organic pigments, and so forth. Two or more of these may be used in combination. The content of the colorant in the cosmetic product is preferably 0.1 to 5 mass % of the total mass of the cosmetic product.

The content of the amino acid-modified organopolysiloxane emulsion of the present invention in a cosmetic product, and the content in a cosmetic product of the above-described cosmetic ingredients that are typically used in cosmetic products will vary as a function of the type, application, attributes, properties, and so forth, of the cosmetic product and so are not particularly limited. Accordingly, the content of the amino acid-modified organopolysiloxane emulsion in a cosmetic product can be established as appropriate in the range of 0.1 to 99.9 mass %, 1 to 99 mass % 10 to 90 mass %, 20 to 80 mass %, 30 to 70 mass %, 40 to 60 mass %, and so forth. Thus, in the case, for example, of a cosmetic product consisting only of fragrance, colorant, and the amino acid-modified organopolysiloxane of the present invention, the content of the amino acid-modified organopolysiloxane emulsion can exceed 99 mass %.

The form and properties of cosmetic products that incorporate the amino acid-modified organopolysiloxane emulsion of the present invention are not particularly limited. However, cosmetic products having the form of an oil-in-water emulsion are preferred, and an oil-in-water emulsion cosmetic product in which a continuous aqueous phase has a disperse phase that has a mean particle size, as measured using laser diffraction/scattering, of less than 10.0 μm or less than 0.5 μm (500 nm) and particularly less than 0.2 μm (200 nm) is particularly preferred. An oil-in-water emulsion cosmetic product having a mean particle size less than 0.5 μm presents a translucent to milky appearance, and offers the advantage of particularly good stability over time.

A cosmetic product having the form of an oil-in-water emulsion can be obtained by mixing a desired amount of water, using a known stirring device or mixing device or emulsifying device (e.g., a paddle-equipped stirrer, propeller stirrer, Henschel mixer, TK Homo Mixer (Tokushu Kika Kogyo Kabushiki Kaisha), TK Homo Disper (Tokushu Kika Kogyo Kabushiki Kaisha), and so forth), with the aforementioned cosmetic ingredients generally used in cosmetic products, and the amino acid-modified organopolysiloxane emulsion of the present invention. While a high shear force emulsifying device, such as a colloid mill or colloid mixer, or a high-pressure emulsifying device as described above is not necessarily required for this mixing, the use of such devices is preferred because they enable the acquisition of a stable oil-in-water emulsion having small to microscopic particle sizes.

A cosmetic product having the form of an oil-in-water emulsion can be prepared, for example, by first mixing the components that make up the disperse phase to homogeneity to prepare a preliminary mixture. Then, while stirring the water and components making up the aqueous phase at about 500 to 5000 rpm, this preliminary mixture and the amino acid-modified organopolysiloxane emulsion of the present invention are gradually added in any sequence, and stirring is continued after addition. The mass ratio of the water with respect to the preliminary mixture may be freely selected. However, 0.05/0.95 to 0.50/0.50 is advantageous from the standpoint of the stability over time of the obtained oil-in-water emulsion cosmetic product. When only a small amount of the cosmetic product is to be produced, for example, the preliminary mixture and amino acid-modified organopolysiloxane emulsion of the present invention may be gradually added while manually stirring, using, for example, a spatula, the water and components constituting the aqueous phase in a freely selected container.

The investigation of the emulsification conditions that are generally required for the production of a stable oil-in-water emulsion is easy for an oil-in-water cosmetic product that incorporates the amino acid-modified organopolysiloxane emulsion of the present invention. Moreover, such a cosmetic product exhibits excellent stability with time and an excellent use sensation.

The water used to produce a cosmetic product having the form of an oil-in-water emulsion completely integrates with the water present in the amino acid-modified organopolysiloxane emulsion of the present invention, and the two therefore cannot be distinguished in the cosmetic product.

The use of the amino acid-modified organopolysiloxane emulsion of the present invention thus enables the production, without the use of a special emulsifying device, of a cosmetic product having the form of an oil-in-water emulsion that has a disperse phase with a microfine particle size. Moreover, the resulting cosmetic product exhibits excellent stability over time. The amino acid-modified organopolysiloxane emulsion of the present invention preferably accounts for 5 to 50 mass % of the cosmetic product in the case of a cosmetic product having the form of an oil-in-water emulsion.

INDUSTRIAL APPLICABILITY

The applications of the above-described cosmetic products are not particularly limited, and include skin cosmetic products, such as skin cleansing products, skin care products, make-up products, antiperspirants, UV protectants, and so forth; hair cosmetic products, such as hair cleansing products, hair styling products, hair dyeing products, hair maintenance products, hair rinse products, and so forth; bath cosmetic products; and perfumed water and colognes. Skin cosmetic products and hair cosmetic products are particularly preferred as cosmetic products incorporating the amino acid-modified organopolysiloxane emulsion of the present invention.

The skin cosmetics may be used at any location, such as on the scalp, face (including the lips, eyebrows, and cheeks), fingers, nails, and whole body. The skin cosmetics can be specifically exemplified by skin cleansing products such as cleansing gel, cleansing cream, cleansing foam, cleansing milk, cleansing lotion, facial cleansing cream, eye make-up remover, facial cleansing foam, liquid whole-body soap, hand soap, gel soap, bar soap, facial rinse, body rinse, shaving cream, nail polish remover, anti-acne products, and so forth; skin care products such as skin cream, scalp treatments, skin milk, milk lotion, lotions, serum, moisturizers, beautifying liquids, facial packs, body powder, body lotions, essences, shaving lotions, and so forth; make-up cosmetics such as foundation, make-up base, white powder, face powder, loose and compact or pressed powder, lipstick, lip cream, lip color, lip gloss, eye shadow, eyeliner, eye cream, eyebrow pencil, eyebrow brush, mascara, rouge, cheek cosmetic products (cheek color, cheek rouge), nail polish, toe polish, nail color, nail lacquer, enamel remover, nail buffers, and so forth; deodorants and other antiperspirants; and UV protectants such as sunscreen, suntanning preparations (suntanning agents), and so forth.

The aforementioned hair cosmetic can be specifically exemplified by hair cleansing agents such as shampoo, conditioning shampoo, and so forth; hair styling products such as hair oil, hair serum, relaxers, hair curl retaining agents, setting agents, hair cream, hair spray, mousse, styling gel, hair wax, hair pomade, hair liquid, and so forth; hair coloring products such as hair dye, including permanent, semi-permanent, demi-permanent and temporary, hair color spray, hair color rinse, hair color stick, and so forth; hair maintenance products such as leave-in conditioners, hair tonic, hair treatment, hair packs, and so forth; hair rinse products such as conditioner, oil rinse, cream rinse, treatment rinse, and so forth; and eyelash cosmetic products such as mascara and so forth.

The aforementioned bath cosmetic products can be exemplified by bath oil, bath salts, and foam bath products.

The container holding the cosmetic product as described above is not particularly limited, and can be exemplified by jars, pumps, tubes, bottles, pressure spray containers, pressure-resistant aerosol containers, light-resistant containers, compact containers, metal cans, lipstick containers, dispensing containers, atomizer containers, partitioned containers with mixed fluid discharge outlets, and so forth. The container can be exemplified by jars, pumps, bottles, atomizer containers, and so forth in the case of oil-in-water emulsion cosmetics. Due to the excellent stability over time of oil-in-water emulsion cosmetics produced using the amino acid-modified organopolysiloxane emulsion of the present invention, such a cosmetic can be held in a stable manner even when contained in a transparent container, and, as a product with an excellent appearance, it will then exhibit an excellent consumer appeal. Benefits of the amino acid-modified organopolysiloxane emulsions may include but are not limited to moisturization, shine, conditioning benefits including wet and dry combing, sensations on the hair and skin, such as smoothness and suppleness, foam quantity, foam generation, ease of rinse, and a low degree of tackiness.

EXAMPLES

The invention will be described in more detail by way of examples, which however should not be construed as limiting the scope of the invention. In the subsequent examples, "part(s)" means part(s) by weight.

[Synthesis of Epoxy-Modified Silicone]

Synthesis Example 1

83.4 g polysiloxane having hydrogen at both terminals and represented by the following formula:

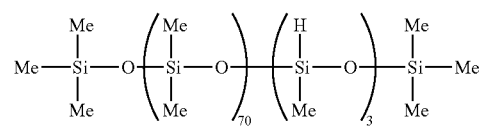

(Me in the formula represents a methyl group), 16.6 g epoxy-functional allyl polyether represented by the following formula:

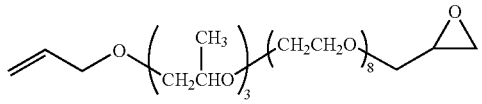

and 0.05 g methanolic sodium acetate solution were mixed, and heated to 50° C. 0.02 g platinum catalyst was added, and a reaction was carried out for 3 hours at 80° C. to 90° C. The low boilers were then distilled out under reduced pressure to yield 100 g epoxy polyether-modified silicone represented by the following formula:

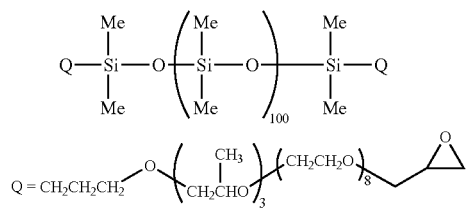

(Me in the formula represents a methyl group).

Synthesis Example 2

73.1 g polysiloxane having hydrogen at the side chains, and represented by the following formula:

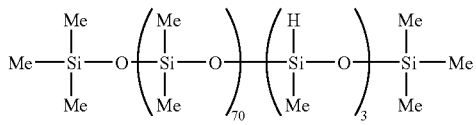

(Me in the formula represents a methyl group), 26.9 g epoxy-functional allyl polyether represented by the following formula:

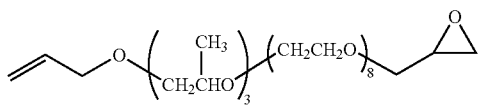

and 0.05 g methanolic sodium acetate solution were mixed, and heated to 50° C. 0.02 g platinum catalyst was added, and a reaction was carried out for 3 hours at 80° C. to 90° C. The low boilers were then distilled out under reduced pressure to yield 100 g epoxy polyether-modified silicone represented by the following formula:

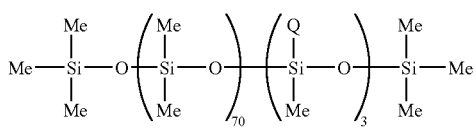

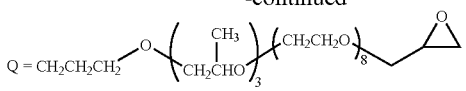

(Me in the formula represents a methyl group).

Synthesis Example 3

83.4 g polysiloxane having pendant hydrogen atoms and represented by the following formula:

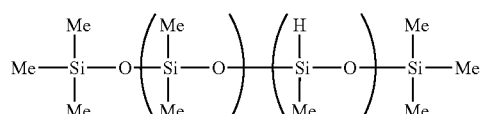

(Me in the formula represents a methyl group), 16.6 g epoxy-functional allyl polyether represented by the following formula:

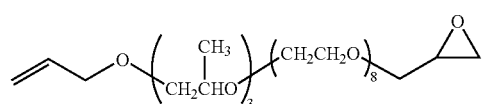

and 0.05 g methanolic sodium acetate solution were mixed, and heated to 50° C. 0.02 g platinum catalyst was added, and a reaction was carried out for 3 hours at 80° C. to 90° C. The low boilers were then distilled out under reduced pressure to yield 100 g epoxy polyether-modified silicone represented by the following formula:

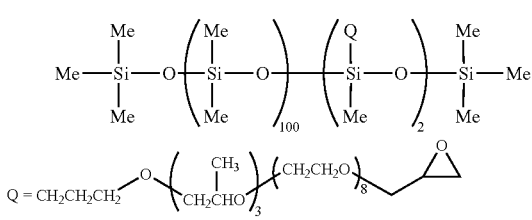

(Me in the formula represents a methyl group).

[Preparation of Basic Amino Acid-Modified Silicone Emulsions]

Example 1

25 parts of the epoxy polyether-modified silicone of Synthesis Example 2, 4.7 parts of polyoxyethylene(25)laurylether, and 2.3 parts of polyoxyethylene(4)laurylether were stirred; 1 part of water was added; and emulsification was carried out. 0.4 parts of sodium benzoate, 1.8 parts of L-arginine, and 59.0 parts of water were then added and emulsified. An emulsion was prepared by carrying out the reaction for 5 hours at 50° C. to 60° C. The product was extracted from the resulting emulsion using alcohol and analyzed by $^1$H-NMR: a peak for an epoxy group originating from the epoxy polyether-modified silicone was not detected.

Example 2

25 parts of the epoxy polyether-modified silicone of Synthesis Example 1, 3.1 parts of polyoxyethylene(25)laurylether, and 3.5 parts of polyoxyethylene(4)laurylether were stirred; 1 part of water was added; and emulsification was carried out. 0.4 parts of sodium benzoate, 0.9 parts of L-arginine, and 60.3 parts of water were then added and emulsified. An emulsion was prepared by carrying out the reaction for 5 hours at 50° C. to 60° C. The product was extracted from the resulting emulsion using alcohol and analyzed by $^1$H-NMR: a peak for an epoxy group originating from the epoxy polyether-modified silicone was not detected.

Example 3

25 parts of the epoxy polyether-modified silicone of Synthesis Example 3, 3.1 parts of polyoxyethylene(25)laurylether, and 3.5 parts of polyoxyethylene(4)laurylether were stirred; 1 part of water was added; and emulsification was carried out. 0.4 parts of sodium benzoate, 1.2 parts of L-arginine, and 60.0 parts of water were then added and emulsified. An emulsion was prepared by carrying out the reaction for 5 hours at 50° C. to 60° C. The product was extracted from the resulting emulsion using alcohol and analyzed by $^1$H-NMR: a peak for an epoxy group originating from the epoxy polyether-modified silicone was not detected.

[Evaluation]
(Wet Comb-Through Properties)

To obtain a sample, an untreated hair tress (obtained from an Asian individual) with a length of approximately 27 cm and a weight of approximately 2 g was washed with a silicone-free shampoo, thoroughly rinsed, and the excess water was removed with a towel. This was then suspended, and was spontaneously dried for 24 hours at room temperature to yield the sample.

The emulsions prepared in Examples 1 to 3 were respectively directly applied to three samples. Then, each of the samples was impregnated with water. Thereafter, it was combed while wet, and the comb-through time was measured. In Comparative Examples 1 and 2, the comb-through time was measured for a sample to which water had been applied instead of the emulsion from Examples 1 to 3, and for a sample to which a cystine-modified polysiloxane emulsion (Crodasone Cystine from Croda Personal Care) had been applied instead of the emulsion from Examples 1 to 3. The results are reported in FIG. 1.

As is clear from FIG. 1, the samples to which the emulsion from Examples 1 to 3 was applied have a shorter comb-through time than the samples in Comparative Examples 1 and 2. The emulsion of the present invention therefore exhibits excellent wet comb-through performance, and can be very suitably used as a component in cosmetic products.

(Static Characteristics)

The emulsions from Examples 1 to 3 were respectively directly applied to three samples. A sample to which water had been applied and a sample to which a cystine-modified polysiloxane emulsion (Crodasone Cystine from Croda Personal Care) had been applied were used, respectively, in Comparative Examples 1 and 2. The samples of Examples 1 to 3 and Comparative Examples 1 and 2 were hung, and brushed for the same number of times from the roots to the ends of the sample to charge the hair, and the maximum value of the angle of hair spread was then measured for each sample.

The spread angle for the samples of Examples 1 to 3 was about 5 to 10°, while the spread angle for Comparative Example 1 was 18° and the spread angle for Comparative Example 2 was 24°. These results show that the emulsion of the present invention exhibits an excellent capacity to prevent static electrification, and is thus valuable as a cosmetic product component.

[Moisturizing Effect]

The skin moisturizing effect of Examples 1 to 3 was assessed by the following method.

5 female panelists washed their forearms with silicone free soap. Then, a sample was applied randomly onto a test site (a rectangle of 4 cm×9 cm) on one of the arms. The skin moisturization on the test site was measured with the CORNEOMETER MPA 5 electric GmbH (manufactured by Courage+Khazaka Co.) by comparing the test site with a control site (neat area) on the skin. The measured value was an average of the values at six points in the test site.

Figure 2:
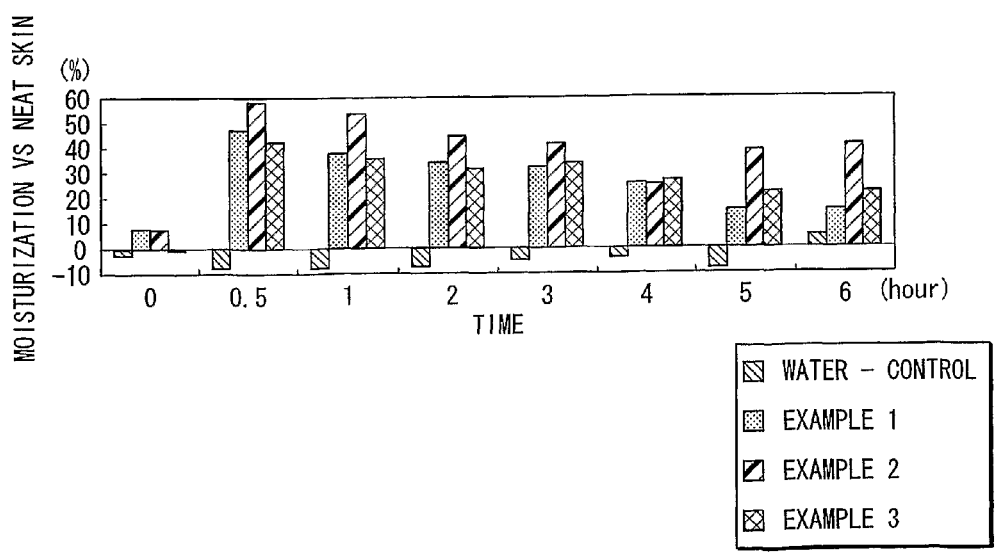
FIG. 2 is a graph showing the results of the evaluation of the moisturizing effects of Examples 1 to 3 and the Control.

(1) 0.020 g of the emulsions of Examples 1 to 3, and water (control) were applied to human skins in accordance with the above method, and those moisturizing effects were measured just after applying, after 0.5 Hr, 1.0 Hr, 2.0 Hr, 3.0 Hr, 4.0 Hr, 5.0 Hr and 6.0 Hr. The results are reported in FIG. 2.

Figure 3:
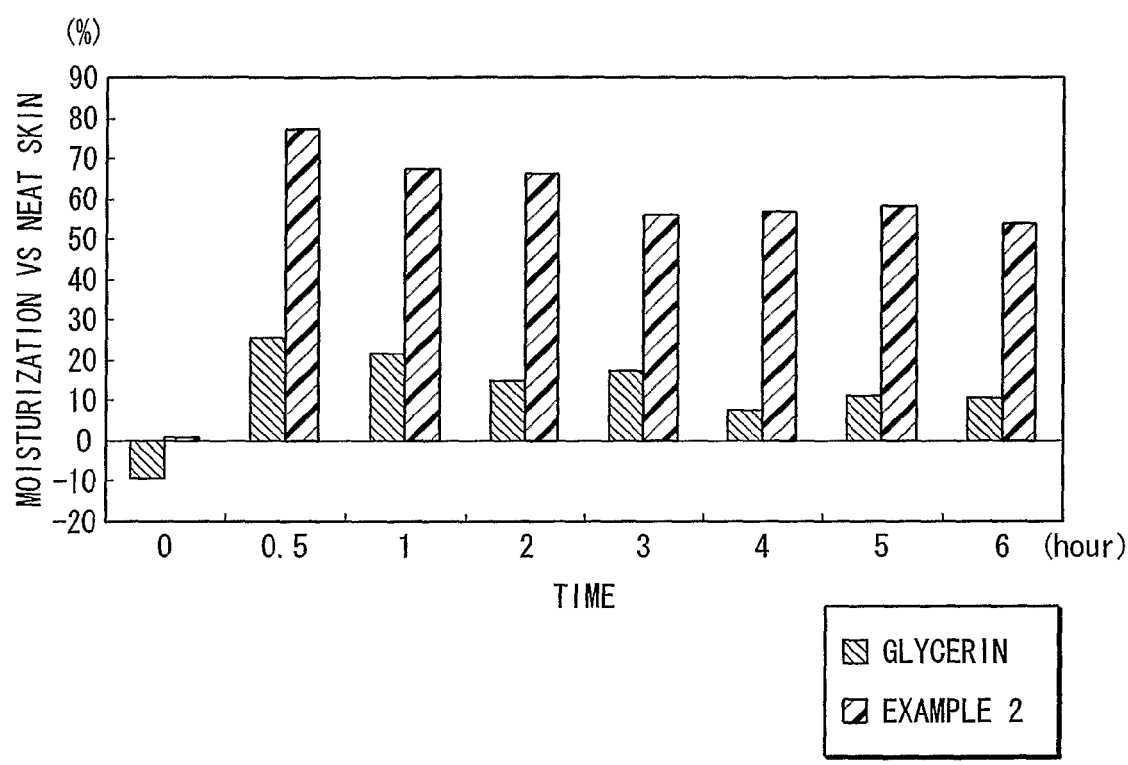
FIG. 3 is a graph showing the results of the evaluation of the moisturizing effects of Example 2 and a 5% glycerin aqueous solution.

(2) 0.020 g of the emulsion of Example 2, and a 5% glycerin solution (control) were applied to human skins in accordance with the above method, and those moisturizing effects were measured just after applying, after 0.5 Hr 1.0 Hr, 2.0 Hr, 3.0 Hr, 4.0 Hr, 5.0 Hr and 6.0 Hr. The results are reported in FIG. 3.

(Skin Cosmetic: Preparation and Evaluation of Shower Gel)

Shower Gel 1 and Shower Gel 2, with the formulations as shown in Table 1, as well as Shower Gel 3 (control) were prepared by the below production procedure.

TABLE 1

| | | formulation Shower Gel No. | | |
| --- | --- | --- | --- | --- |
| Component | | 1 (%) | 2 (%) | 3 (%) |
| 1 | sodium polyoxyethylene lauryl ether sulfate | 30.00 | 30.00 | 30.00 |
| 2 | decylglucoside | 5.00 | 5.00 | 5.00 |
| 3 | cocofatty acid amidopropyldimethylbetaine | 10.00 | 10.00 | 10.00 |
| 4 | polyoxyethylene lauryl ether | 2.00 | 2.00 | 2.00 |
| 5 | Polyacrylamide | 2.00 | 2.00 | 2.00 |
| 6 (1) | Emulsion of Example 1 | 18.50 | — | — |
| 6 (2) | Emulsion of Example 2 | — | 19.30 | — |
| 7 | ion-exchanged water | 32.50 | 31.70 | 51.00 |
| 8 | citric acid | qs | qs | qs |

(Production Procedure)

Components 1 through 3 were mixed, and the resulting mixture was added to a previously prepared mixture of Components 4, 5, and 6(1) or 6(2) while stirring. Components 7 and 8 were subsequently added, the pH was adjusted to 6, and a shower gel was then produced by stirring.

Comparing the shower gels (Shower Gels 1 and 2) corresponding to the examples of the present invention with the control (Shower Gel 3), it was found that these of the present invention exhibit remarkably excellent properties over the control in terms of foaming, foam quality, rinsing, and stickiness.

[Sensory Evaluation]

The sensory evaluation of the shower gels was performed by 18 panelists, according to the following procedure:
1. Each panelist rinsed the left and right hands, and their respective forearms for 8 seconds.

2. 3 ml of the shower gel according to the present invention as well as 3 ml of Shower Gel 3 (control) were taken, and applied them onto the hand and forearm, and the panelist lathered both for 20 seconds.
3. For foaming, the panelist determined which showed more rapid foaming
4. For foam quality, the panelist determined which formed creamy foam with better texture.
5. The panelist rinsed the right and left hands and forearms.
6. For rinsing, the panelist determined which was easier to rinse.
7. The panelist wiped the right and left hands and forearms with a paper towel to remove excess water.
8. After 2 minutes, for stickiness, the panelist determined which was less sticky.

Table 2 shows the results of the evaluation by 18 panelists on each item, using the shower gels (Shower Gels 1 and 2) corresponding to the examples of the present invention. The number in the table shows the number of panelists who determined that the shower gels corresponding to the examples of the present invention exhibited better effects than the control.

TABLE 2

| Shower gel No. | 1 | 2 |
|---|---|---|
| Foaming | 12 | 16 |
| Foam quality | 11 | 6 |
| Rinsing | 7 | 15 |
| Stickiness | 9 | 14 |

As shown in Table 2, the shower gels comprising the emulsion composition according to the present invention were evaluated as comparable to or better than the control, in terms of foaming, foam quality, rinsing, and stickiness.

Examples of formulation for cosmetic products of the present invention are given below.

Formulation Example 1

Conditioner

Components

| 1. ion-exchanged water | balance |
|---|---|
| 2. hydroxyethyl cellulose | 1.5 parts |
| 3. Cetearyl alcohol | 1.0 part |
| 4. mixture of PEG-100 stearate and glyceryl stearate | 1.0 part |
| 5. emulsion of Example 1 | 7.7 parts |
| 6. preservative | suitable amount |
| 7. citric acid | suitable amount |

(Production Procedure)

Components 1 and 2 were stirred at 75° C. to bring about the complete dissolution of component 2. After cooling this to 60° C., components 3 and 4 were then added while stirring. This was followed by cooling to 40° C., the addition of component 5, and stirring for 5 to 10 minutes. Components 6 and 7 were thereafter added and the pH was adjusted to 6 to 7 to give the conditioner. The conditioner produced using this recipe gave excellent wet and dry comb-through performances and provided an excellent tactile sensation.

Formulation Example 2

Shampoo

Components

| 1. ion-exchanged water | balance |
|---|---|
| 2. O-[2-hydroxy-3-(trimethylammonio)propyl]-hydroxyethyl cellulose chloride | 0.3 part |
| 3. PEG-150 pentaerythrityl tetrastearate | 7.0 parts |
| 4. sodium polyoxyethylene lauryl ether sulfate | 30 parts |
| 5. cocofatty acid, monoethanolamide | 3.0 parts |
| 6. cocamidopropyl betaine | 3.0 parts |
| 7. emulsion of Example 1 | 7.7 parts |
| 8. citric acid | suitable amount |
| 9. preservative | suitable amount |

(Production Procedure)

Components 1 and 2 were mixed to bring about the complete dissolution of component 2. This was followed by heating to 75° C. and the addition of component 3 while stirring. This was followed by cooling to 40° C. and then components 4 to 6 were added sequentially while stirring. This was followed by the addition of component 7 and stirring for 5 to 10 minutes. Components 8 and 9 were subsequently added while stirring to yield the shampoo. Hair treated with shampoo obtained using this recipe gave excellent wet and dry comb-through performances and provided an excellent tactile sensation.

Formulation Example 3

Shower Gel

Components

| 1. sodium polyoxyethylene lauryl ether sulfate | 30 parts |
|---|---|
| 2. decylglucoside | 5 parts |
| 3. cocofatty acid amidopropyldimethylbetaine | 10 parts |
| 4. polyoxyethylene lauryl ether | 2 parts |
| 5. polyacrylamide | 2 parts |
| 6. emulsion of Example 3 | 19.3 parts |
| 7. ion-exchanged water | balance |
| 8. citric acid | suitable amount |

(Production Procedure)

Components 1 through 3 were mixed, and to this mixture a preliminarily prepared mixture of components 4 through 6 was added while stirring. Components 7 and 8 were subsequently added, the pH was adjusted to 6, and the shower gel was then produced by stirring. The gel obtained using this recipe exhibits excellent foaming and rinsing properties and an excellent tactile sensation.

The invention claimed is:
1. A method of producing an amino acid-modified organopolysiloxane emulsion, characterized by reacting
   (a) a carboxy-unprotected amino acid and
   (b) organopolysiloxane that has an epoxy group in the molecule in an aqueous medium in the presence of a surfactant;
   wherein the carboxy-unprotected amino acid (a) is a basic amino acid selected from the group consisting of lysine, arginine, and histidine.

2. The method according to claim 1, wherein the carboxy-unprotected amino acid (a) is arginine as represented by the following formula:

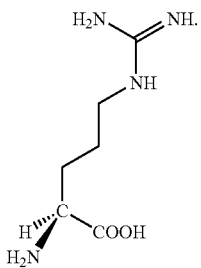 [SMILES: N=C(N)NCCC[C@H](N)C(=O)O]

3. The method according to claim 1, wherein the organopolysiloxane that has an epoxy group in the molecule (b) is organopolysiloxane represented by the following general formula (1):

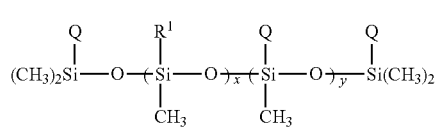
(1)

{wherein
each $R^1$ independently represents unsubstituted or substituted alkyl, unsubstituted or substituted aryl, unsubstituted or substituted aralkyl, unsubstituted or substituted alkoxy, an unsubstituted or substituted polyether group, hydroxyl, -A—NH—B—NH$_2$, -A—N(—B—NH$_2$)$_2$, or —CH$_2$CH$_2$Si(CH$_3$)$_2$—{OSi(CH$_3$)$_2$}$_t$—OSi(CH$_3$)$_3$ (in these formulas, A and B each independently represent unsubstituted or substituted alkylene or —C$_u$H$_{2u}$—O—C$_v$H$_{2v}$— (u and v each independently represent an integer in the range from 1 to 5) and t represents an integer in the range from 0 to 500);
Q is a group represented by the following formula:

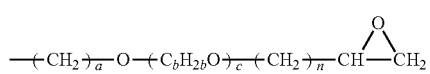

(wherein a represents an integer in the range from 1 to 20, b represents an integer in the range from 1 to 10, c represents an integer in the range from 0 to 50, and n represents an integer in the range from 1 to 20), or represents a group as defined for $R^1$ above, with the proviso that all of the Q groups are not $R^1$;
x represents an integer in the range from 1 to 10000; and
y represents an integer in the range from 0 to 1000},
or is represented by the following general formula (2):

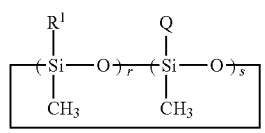
(2)

(wherein
$R^1$ and Q are defined as above;
r represents an integer in the range from 1 to 10;
s represents an integer in the range from 1 to 10; and
r +s represents an integer in the range from 3 to 20).

4. The method according to claim 3, wherein the organopolysiloxane that has an epoxy group in the molecule (b) is organopolysiloxane that has an epoxy group and an ether chain in the molecule and is represented by the following general formula (1'):

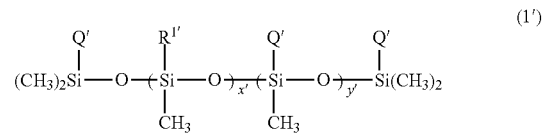
(1')

{wherein
each $R^{1'}$ independently represents unsubstituted or substituted $C_{1-20}$ alkyl, unsubstituted or substituted $C_{6-20}$ aryl, unsubstituted or substituted $C_{7-20}$ aralkyl, or hydroxyl;
Q' is a group represented by

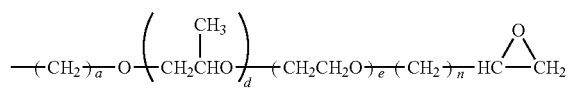

(wherein
n and a are defined as above,
d represents an integer in the range from 0 to 10, and
e represents an integer in the range from 0 to 10), or represents a group as defined for $R^{1'}$ above, with the proviso that all of the Q' groups are not $R^{1'}$;
x' represents an integer in the range from 5 to 1000; and
y' represents an integer in the range from 0 to 100}.

5. The method according to claim 1, wherein the surfactant is selected from the group consisting of nonionic surfactants, anionic surfactants, and their mixtures.

6. The method according to claim 1, wherein the surfactant is selected from the group consisting of nonionic surfactants, cationic surfactants, and their mixtures.

7. An amino acid-modified organopolysiloxane emulsion comprising:
(A) An amino acid-modified organopolysiloxane represented by the following general formula (3'):

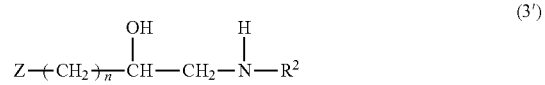
(3')

{wherein
Z represents an organopolysiloxane residue;
$R^2$ represents
—CH(COOH)—(CH$_2$)$_3$—NH—C(=NH)—NH$_2$,
—C(=NH)—NH—(CH$_2$)$_3$—CH(COOH)—NH$_2$,
—CH(COOH)—(CH$_2$)$_3$—N(—CH$_2$—CH(OH)—(CH$_2$)$_{n'}$—Z')—C(=NH)—NH$_2$,
—C(=NH)—N(—CH$_2$—CH(OH)—(CH$_2$)$_{n'}$—Z')—(CH$_2$)$_3$—CH(COOH)—NH$_2$,
—C(=NH)—NH—(CH$_2$)$_3$—CH(COOH)—NH—CH$_2$—CH(OH)—(CH$_2$)$_{n'}$—Z', —CH(COOH)—(CH₂)₃—N(—CH₂—CH(OH)
—(CH₂)$_{n'}$—Z')—C(=NH)—NH—CH(OH)—CH₂)$_{n''}$
—Z'',
—C(=NH)—NH—(CH₂)₃—CH(COOH)—N(—CH₂—
CH(OH)—(CH₂)$_{n'}$—Z')—CH₂—CH(OH)—(CH₂)$_{n''}$
—Z'',
—CH(COOH)—(CH₂)₃—NH—C(=NH)—N(—CH₂—
CH(OH)—(CH₂)$_{n'}$—Z')—CH(OH)—(CH₂)$_{n'}$—Z'',
—C(=NH)—N(—CH₂—CH(OH)—(CH₂)$_{n'}$—Z''')—
(CH₂)₃—CH(COOH)—N(—CH₂—CH(OH)
—(CH₂)$_{n'}$—Z')—CH₂—CH(OH)—(CH₂)$_{n''}$—Z'',
—CH(COOH)—(CH₂)₃—N(—CH₂—CH(OH)
—(CH₂)$_{n'''}$ —Z''')—C(=NH)—N(—CH₂—CH
(OH)—(CH₂)$_{n'}$—Z')—CH(OH)—(CH₂)$_{n''}$—Z'',
—(CH₂)₄—CH(NH₂)COOH,
—CH(COOH)—(CH₂)₄—NH₂,
—(CH₂)₄—CH(NH—CH₂—CH(OH)—(CH₂)$_{n'}$—Z')
COOH,
—(CH₂)₄—CH(N(—CH₂—CH(OH)—(CH₂)$_{n'}$—Z')—
CH₂—CH(OH)—(CH₂)$_{n''}$—Z''),
—CH(COOH)—(CH₂)₄—N(—CH₂—CH(OH)
—(CH₂)$_{n'}$—Z')—CH₂—CH(OH)—(CH₂)$_{n''}$—Z'', or
—CH(COOH)—CH₂—imidazolyl
(wherein in the preceding formulas
Z', Z'', and Z''' each independently represent an organopolysiloxane residue, and
n', n'', and n''' each independently represent an integer in the range from 1 to 20; and
n is defined as above},
or the following general formula (4'):

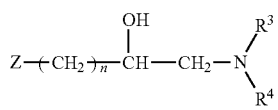

(4')

{wherein
Z is defined as above;
R³ represents
—CH(COOH)—(CH₂)₃—NH—C(=NH)—NH₂,
—C(=NH)—NH—(CH₂)₃—CH(COOH)—NH₂,
—(CH₂)₃—CH(COOH)—NH₂,
—CH(COOH)—(CH₂)₃—N(—CH₂—CH(OH)
—(CH₂)$_{n'}$—Z')—C(=NH)—NH₂,
—C(=NH)—N(—CH₂—CH(OH)—(CH₂)$_{n'}$—Z')—
(CH₂)₃—CH(COOH)—NH₂,
—CH(COOH)—(CH₂)₃—NH—C(=NH)—N(—CH₂—
CH(OH)—(CH₂)$_{n'}$—Z')—CH₂—CH(OH)—(CH₂)$_{n''}$
—Z'',
—C(=NH)—N(—CH₂—CH(OH)—(CH₂)$_{n'}$—Z')—
(CH₂)₃—CH(COOH)—N(—CH₂—CH(OH)
—(CH₂)$_{n''}$ —Z'')—CH₂—CH(OH)—(CH₂)$_{n'''}$—Z''',
—(CH₂)₂₄—CH(NH₂)COOH,
—CH(COOH)—(CH₂)₄—NH₂,
—CH(COOH)—(CH₂)₄—N(—CH₂—CH(OH)
—(CH₂)$_{n'}$—Z')—CH₂—CH(OH)—(CH₂)$_{n''}$—Z'', or
—CH(COOH)—CH₂—imidazolyl
(wherein in the preceding formulas Z', Z'', and Z''' and n', n'', and n''' are defined as above);
R⁴ represents
—C(=NH)—NH₂ or
—CH₂—CH(OH)—(CH₂)$_{n''''}$—Z''''

(wherein
Z'''' represents a polysiloxane residue, and
n'''' represents an integer in the range from 1 to 20); and
n is defined as above},
or the following general formula (5'):

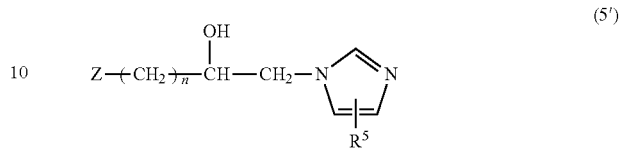

(5')

{wherein
Z is defined as above;
R⁵ represents
—CH₂—CH(NH₂)COOH,
—CH₂—CH(NH(—CH₂—CH(OH)—(CH₂)$_{n'}$—Z'))
COOH, or
—CH₂—CH(N(—CH₂—CH(OH)—(CH₂)$_{n'}$—Z')—
CH₂—CH(OH)—(CH₂)$_{n''}$Z'')COOH
(wherein in the preceding formulas
Z' and Z'' and n' and n'' are defined as above); and
n is defined as above};
(B) surfactant; and
(C) water.

8. The amino acid-modified organopolysiloxane emulsion according to claim 7, wherein the organopolysiloxane residue is represented by the following general formula (6):

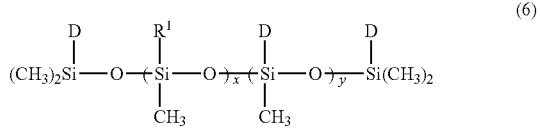

(6)

{wherein
R¹ represents unsubstituted or substituted alkyl, unsubstituted or substituted aryl, unsubstituted or substituted aralkyl, unsubstituted or substituted alkoxy, an unsubstituted or substituted polyether group, hydroxyl, -A-NH—B—NH₂, -A-N(—B—NH₂)₂, or —CH₂CH₂Si(CH₃)₂—{OSi(CH₃)₂}$_t$—OSi(CH₃)₃ (in these formulas, A and B each independently represent unsubstituted or substituted alkylene or —C$_u$H$_{2u}$—O—C$_v$H$_{2v}$-(u and v each independently represent an integer in the range from 1 to 5) and t represents an integer in the range from 0 to 500);
D represents —(CH₂)$_a$—O—(C$_b$H$_{2b}$O)$_c$— (wherein a represents an integer in the range from 1 to 20, b represents an integer in the range from 1 to 10, c represents an integer in the range from 0 to 50), or a group as defined for R¹ above, with the proviso that all of the D groups are not R¹;
x represents an integer in the range from 1 to 10000; and
y represents an integer in the range from 0 to 1000);}, or
wherein the organopolysiloxane residue is represented by the following general formula (7):

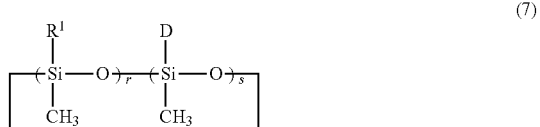

(7)

(wherein $R^1$ and D are defined as above;

r represents an integer in the range from 1 to 10;

s represents an integer in the range from 1 to 10; and r+s represents an integer in the range from 3 to 20).

9. The amino acid-modified organopolysiloxane emulsion according to claim 8, wherein the amino acid-modified organopolysiloxane (A) has in the molecule at least one moiety represented by the following formula (3″), (4″), or (5″):

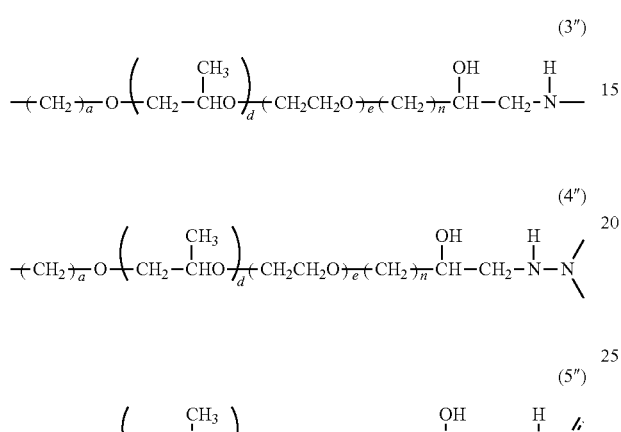

(n in these formulas is defined as above;

a represents an integer in the range from 1 to 20;

d represents an integer in the range from 0 to 10; and e represents an integer in the range from 1 to 10).

10. The amino acid-modified organopolysiloxane emulsion according to claim 9, wherein the amino acid-modified organopolysiloxane (A) is an arginine-modified organopolysiloxane represented by the following general formula (8):

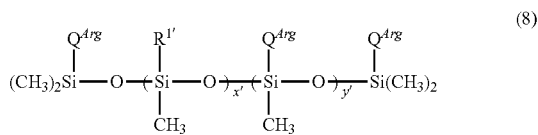

{wherein $R^{1'}$ is defined as above;

$Q^{Arg}$ is a group represented by the following formula:

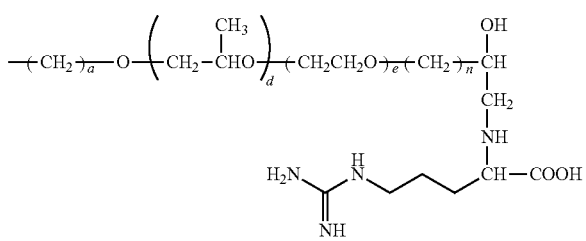

(wherein n, a, d, and e are defined as above), or represents a group as defined for $R^{1'}$ above, with the proviso that all of the $Q^{Arg}$ groups are not $R^{1'}$;

x' represents an integer in the range from 5 to 1000; and y' represents an integer in the range from 0 to 100}.

11. The amino acid-modified organopolysiloxane emulsion according to claim 7, comprising 1 to 100 parts by weight of the surfactant (B) and 10 to 10,000 parts by weight of water (C), in each case with reference to 100 parts by weight of the amino acid-modified organopolysiloxane (A).

12. A cosmetic product that comprises an amino acid-modified organopolysiloxane emulsion according to claim 7.

\* \* \* \* \*